US011458264B2

(12) United States Patent
Clements

(10) Patent No.: US 11,458,264 B2
(45) Date of Patent: *Oct. 4, 2022

(54) VALVED FLEXIBLE BAG SPACER DEVICE FOR A NEBULIZER

(71) Applicant: Inspiring Pty Ltd, Dalkeith (AU)

(72) Inventor: Barry Spencer Clements, Dalkeith (AU)

(73) Assignee: Inspiring Pty Ltd, Dalkeith (AU)

( * ) Notice: Subject to any disclaimer, the term of this patent is extended or adjusted under 35 U.S.C. 154(b) by 269 days.

This patent is subject to a terminal disclaimer.

(21) Appl. No.: 16/606,099

(22) PCT Filed: Apr. 18, 2018

(86) PCT No.: PCT/AU2018/050343
§ 371 (c)(1),
(2) Date: Oct. 17, 2019

(87) PCT Pub. No.: WO2018/191775
PCT Pub. Date: Oct. 25, 2018

(65) Prior Publication Data
US 2021/0001065 A1  Jan. 7, 2021

(30) Foreign Application Priority Data

Apr. 18, 2017 (AU) ................. 2017901412

(51) Int. Cl.
*A61M 15/00* (2006.01)
(52) U.S. Cl.
CPC .... *A61M 15/0086* (2013.01); *A61M 15/0021* (2014.02); *A61M 2205/0216* (2013.01); *A61M 2205/0233* (2013.01); *A61M 2205/59* (2013.01)

(58) Field of Classification Search
CPC .......... A61M 15/0021; A61M 15/0086; A61M 15/0088; A61M 15/009; A61M 2205/0216; A61M 2205/0233
See application file for complete search history.

(56) References Cited

U.S. PATENT DOCUMENTS 3,923,043 A * 12/1975 Yanda ................. A61B 5/091
600/541
4,119,097 A * 10/1978 Spector ................ A62B 7/02
128/205.17

(Continued)

FOREIGN PATENT DOCUMENTS

FR        2940129 A1    6/2010
WO  WO-2008/021451 A2    2/2008
WO  WO-2017/181228 A1   10/2017

OTHER PUBLICATIONS

International Search Report; prepared for application No. PCT/AU2018/050343; authorized officer Vivian Cheung; dated Jun. 29, 2018; 5 pages.

*Primary Examiner* — Kathryn E Ditmer
(74) *Attorney, Agent, or Firm* — Winstead PC

(57) ABSTRACT

Provided is a spacer device (110) for delivery of drugs via a nebuliser device, the spacer device (110) comprising a bag (112) and a body (118) including inlet (114) and opposed outlet (116), the inlet (114) and opposed outlet (116) being provided on, and integral with, the body (118). The body (118) and bag (112) combine to form chamber (120) for receiving aerosolised medication. The inlet (114) and outlet (116) each are in the form of a port that is in fluid flow communication with the chamber (120). The inlet (114) and outlet (116) define, and are separated by, a broad V-formation formed as part of the body (118). The body (118) further includes an elliptical lower perimeter (118.1) defining flange (118.2), for demountably receiving bag (112).

19 Claims, 13 Drawing Sheets

(56) References Cited

U.S. PATENT DOCUMENTS

| | | | | |
|---|---|---|---|---|
| 5,318,016 A * | 6/1994 | Mecikalski | A61M 15/0086 | 128/200.14 |
| 5,613,489 A * | 3/1997 | Miller | A61M 15/0086 | 128/200.14 |
| 5,842,467 A * | 12/1998 | Greco | A61M 16/0078 | 128/200.23 |
| 6,158,428 A * | 12/2000 | Mecikalski | A61M 15/0086 | 128/200.23 |
| 6,390,090 B1 | 5/2002 | Piper | | |
| 6,401,710 B1 * | 6/2002 | Scheuch | A61M 15/0086 | 128/200.21 |
| 6,463,929 B1 * | 10/2002 | Scheuch | A61M 15/0086 | 128/200.22 |
| 7,726,310 B2 * | 6/2010 | Andrus | A61M 15/0088 | 128/205.13 |
| 9,108,011 B2 * | 8/2015 | Wachtel | A61M 15/0086 | |
| 2002/0069870 A1 * | 6/2002 | Farmer | A61M 16/0833 | 128/200.22 |
| 2003/0041859 A1 * | 3/2003 | Abrams | A61M 15/0086 | 128/200.22 |
| 2004/0234610 A1 * | 11/2004 | Hall | A61M 15/0088 | 424/489 |
| 2005/0217667 A1 * | 10/2005 | Dhuper | A61M 15/0086 | 128/200.23 |
| 2006/0260606 A1 * | 11/2006 | Coifman | A61M 15/009 | 128/200.14 |
| 2007/0012360 A1 * | 1/2007 | Flynn | A61M 16/208 | 137/102 |
| 2007/0283954 A1 * | 12/2007 | Dhuper | A61M 15/0088 | 128/203.12 |
| 2008/0035143 A1 * | 2/2008 | Sievers | A61M 11/008 | 128/203.12 |
| 2008/0210225 A1 * | 9/2008 | Geiger | A61M 15/0086 | 128/200.14 |
| 2011/0108025 A1 * | 5/2011 | Fink | A61M 16/105 | 128/200.16 |
| 2011/0132359 A1 * | 6/2011 | Poree | A61M 15/0018 | 128/203.21 |
| 2013/0192597 A1 * | 8/2013 | McKinnon | A61M 16/0078 | 128/203.28 |
| 2013/0276781 A1 * | 10/2013 | Steelman | A61M 15/0023 | 128/203.12 |
| 2014/0230817 A1 * | 8/2014 | Richardson | A61M 15/002 | 128/203.15 |
| 2014/0311483 A1 | 10/2014 | Engelbreth et al. | | |
| 2016/0256641 A1 * | 9/2016 | Lisberg | A61M 15/009 | |
| 2016/0339187 A1 * | 11/2016 | Smaldone | A61M 15/0016 | |

* cited by examiner

VALVED FLEXIBLE BAG SPACER DEVICE FOR A NEBULIZER

TECHNICAL FIELD

The present invention relates to a spacer device for a nebuliser. More particularly, the present invention relates to a spacer device for use during inhalation of medication from a nebuliser drug delivery device.

BACKGROUND ART

The following discussion of the background art is intended to facilitate an understanding of the present invention only. The discussion is not an acknowledgement or admission that any of the material referred to is or was part of the common general knowledge as at the priority date of the application.

A nebuliser is an inhalant drug delivery device (IDDD) used to administer medication in the form of a mist or microdispersion droplets inhaled into the lungs. Nebulisers are commonly used for the treatment of cystic fibrosis, asthma, Chronic Obstructive Pulmonary Disease (COPD), and other respiratory disease or disorders. Nebulisers use oxygen, compressed air, or ultrasonic power to break up solutions and suspensions containing drugs to be administered into small aerosol droplets that can be directly inhaled from an interface, usually in the form of a mouthpiece (for children over 3 and adults) or a face mask (children under 3 or users that cannot hold a mouthpiece). The definition of an aerosol as used herein is "a mixture of gas and liquid particles".

Nebuliser devices work with either an air compressor or ultrasonic system to deliver the aerosol through a length of tubing via a medication cup (colloquially referred to as a "pot") that contains the drug to be administered. The medication cup is usually fitted directly with a mouthpiece that can easily be received into the mouth of a user. Such mouthpieces are fitted with a one-way release valve for the user's exhaled air—generally in the form of a flap valve located on the upper surface of the mouthpiece. During inhalation, this valve occludes to prevent entrainment of outside air interfering with the flow of aerosol through the mouthpiece from the nebuliser cup into the user's mouth.

The medication to be inhaled is displaced up a capillary tube from the nebuliser's reservoir and is dispersed continuously from the outlet of the medication cup (or nebuliser pot as it is sometimes referred to) as aerosolized particles. Using the mouthpiece (or a mask) attached to this outlet, the aerosolized particles are spontaneously inhaled by the user during normal cyclical breathing.

Nebulisers play an important role in inhalation therapy forming the basis of treatment for many users with respiratory disease. Development of the jet nebuliser almost 60 years ago resulted in a device which is now reliable, portable, and sufficiently standardized to allow successful treatment with inhalation medications at home. These jet nebulisers, still the most commonly used nebulisers today, use the Venturi principle with compressed air or oxygen flowing at high velocity through the nebuliser pot containing the liquid medicine, and turning it into an aerosol which is then inhaled by the user.

Ultrasonic nebulisers are also frequently used today and use the principle of a piezo-electric effect to convert alternating current into high-frequency acoustic energy that converts a solution into aerosolised droplets, typically microdispersion droplets, ready for inhalation. Vibrating mesh nebulisers use a vibrating fenestrated membrane or grid which forces droplets through the small fenestrations forming aerosol. These nebulisers are becoming increasingly popular as they are quiet and efficient producers of aerosol in a shorter space of time although significantly more expensive.

Unfortunately, irrespective of the type of nebuliser used, drug delivery to the lung is generally extremely inefficient with usually less than 30% of the medication inserted into the nebuliser pot reaching the airways of the user. The main reason for this inefficiency is due to aerosol wastage during the exhalation phase of the breathing cycle. Once the nebuliser pump is switched on, the device continuously produces aerosol droplets whilst the user only utilises these droplets during inhalation. All droplets produced while the user is exhaling (at least half the total amount), escape to the outside through the release valve on the mouthpiece accompanying the user's exhaled air—and are wasted.

The inspiratory:expiratory ratio of a normal healthy adult is usually around 1:1 while in children it is around 1:2, which means for every three second breath, one second is spent inhaling and two seconds are spent exhaling. In essence, this simply means that for roughly ⅔ thirds of the time, the nebuliser is producing aerosolised droplets that the user is not inhaling and therefore these droplets are wasted to the atmosphere. This is particularly pertinent when ineffective delivery results in the desired effect not being achieved, or when the inhaled medication is expensive, such as with inhaled gene therapy. Additionally, the 50% or more aerosol escaping to the outside atmosphere during exhalation creates a significant concern regarding environmental contamination, particularly with regards to certain aerosolised medications such as antibiotics.

Recently in an effort to improve efficiency of delivery, so-called intelligent nebulisers were developed which rely on a computer chip to sense pressure changes during breathing and switch the nebuliser off during user exhalation. These devices have been shown to improve delivery up to 80% of the dose now reaching the airways. Unfortunately, however, these devices are extremely expensive, which makes them inaccessible to the average user. In addition, because they only produce aerosol during the inspiratory half of the breathing cycle, the time taken to aerosolise the same dose is doubled.

It is an object of the invention to address the shortcomings of the devices of which the Applicant is aware, and to deliver levels of drug delivery similar to that of intelligent nebulisers without the attendant cost and complexity.

SUMMARY OF THE INVENTION

Broadly, the invention provides for a spacer device for delivery of drugs via a nebuliser device, the spacer device defining a flexible chamber inserted between a nebuliser generator and an outlet of a medication cup.

According to one aspect of the invention, there is provided a spacer device for a nebuliser device, the spacer device including:

a body having an inlet and an outlet opposed from the inlet;

a demountable, flexible bag attached to the body, the bag and body together defining the chamber, such that the inlet and outlet are in fluid flow communication with the chamber;

wherein the inlet is configured for operative connection to a nebuliser device containing a drug to be inhaled;

wherein the outlet is configured to be operatively received by a user's mouth; and wherein the flexible bag serves as a reservoir to allow for the formation therewithin of a cloud or mist of the drug to be inhaled upon activation of the nebuliser device, the flexible bag being configured to be at least partially inflatable and at least partially deflatable commensurate with a breathing pattern of said user, during use.

The body, inlet, outlet, and/or bag may be configured to reduce a static electricity charge, i.e. anti-static characteristics. The body, inlet, outlet, and/or bag may be made of electrically conductive material. The bag may be made of a metallised polymer film or aluminium foil. The body, inlet, outlet, and/or bag may be treated with an anti-static agent.

The inlet may comprise a mount defining an inlet passage for sealingly engaging with the medication cup. As such, the inlet may comprise a mount defining an inlet passage for sealingly engaging with an exit port of the medication cup. The inlet is typically shaped and dimensioned to receive most common nebuliser outlets via friction-fit, or the like.

The inlet passage may be surrounded by a sealing collar configured to seal against the medication cup or the exit port of the medication cup.

The spacer device may be provided with a mouthpiece that is received on, in, or around the outlet.

In one embodiment, the spacer device is valveless. In another embodiment of the invention, the spacer device includes or defines a one-way valve, two-way valve, relief valve, or deflection mechanism to prevent or minimize air exhaled by a user from entering the spacer device or medication cup.

In one embodiment, the outlet may comprise a mouthpiece. Use may be made of commercially available mouthpieces that are provided with commercially available nebuliser devices and which serve to eliminate or minimize the entrainment of exhaled air within the medication cup. Typically, the mouthpiece on, in or around the outlet may be bi-valved, with one valve to control flow between the outlet of the spacer device and the user's mouth, and the other to control flow from the user's mouth to the outside atmosphere, or the like.

As such, the mouthpiece may include a valve in the form of a release flap provided on an operatively upper surface of the mouthpiece, the flap being able to open selectively when the pressure within the mouthpiece exceeds a pre-determined value, such as during exhalation to allow escape of exhaled air to the atmosphere.

In one embodiment, the outlet and/or mouthpiece may comprise a valve having a body including:

an inlet through which medication from a nebuliser, generally via the spacer device, may be received;

an outlet which exits to the atmosphere, and generally operatively to the user's mouth;

a passageway connecting the inlet and outlet; and at least one selectively activatable occlusion member that prevents the flow or entrainment of exhaled air into the spacer device from the outlet when the pressure of the exhaled air entering the outlet exceeds the pressure of the air emanating from a device (such as a nebuliser) entering the inlet of the valve.

The at least one occlusion member may be in the form of a flexible flap of unitary construction, or may comprise two or more flaps working in unison to occlude a passageway defined through the body of the valve. The, or each, flap may be in the form of a soft, flexible filament, fabric, or sheet. The, or each flap, may be attached to the body of the valve. Alternatively, the, or each, flap may be attached to a central spine which serves to bifurcate the passageway defined between the inlet and outlet of the valve body.

The valve body may include at least one escape passage defined therein for the escape of air upon occlusion of the passageway of the body by the occlusion member, i.e. upon activation of the occlusion member when, for example, a user forcefully exhales into a mouthpiece or facemask attached to the outlet of the valve body at a pressure which exceeds that of aerosol or air being voided from the nebuliser.

The at least one escape passage may be in the form of a passage defined within the body that allows for the exit of air through at least one aperture provided within a radially extending formation, typically a collar, that extends at least partially around an outer surface of the body. The at least one aperture may be configured to exit from the valve body in a direction away from the outlet of the valve body, in other words away from the face of a user that may be exhaling into the mouthpiece attached to the outlet of the valve body. Each aperture may be in the form of a slot provided within the radially extending formation. In one embodiment, the radially extending formation may be provided with a plurality of slots that serve to evacuate exhaled air from the mouthpiece to the outside atmosphere. The size, shape, number, and dimension of the slots may be varied or selected to accommodate flow rates of medication, breathing frequency, exhalation force, and the like, to minimize the effects of exhalation and to encourage rebreathing of medication contained within the bag.

Advantageously, in one embodiment of the invention the one or more apertures (i.e. slots) defined within the radially extending formation may have one or more slot-occluding flap members in the form of one or more flexible flap members applied externally to each slot which serve to occlude the apertures or slots during inhalation, and open to allow exhaled air to pass through the apertures and past the flexible flap members, to the exterior environment.

The above described arrangement means that at no stage during breathing (inhalation or exhalation) are any aerosolized or microdispersion droplets, produced by the nebuliser pump, allowed to escape to the exterior environment. These droplets are therefore trapped in a closed-circuit system where the only escape is into the user's oral cavity, on their way to the lungs during inhalation.

Accordingly, the invention extends, in another aspect thereof, to a valve for a spacer device of the invention, the valve comprising a body having an inlet for engaging with an outlet of a spacer device or medication cup, and outlet to be received by a user, the valve body defining a passageway between the inlet and outlet, the valve body having included therein a selectively activatable occlusion member that prevents the flow or entrainment of air into the spacer device from the outlet of the spacer device, wherein the body has at least one air escape passage provided within either: (i) as a single escape hole on the upper surface of the body covered by a simple flap mechanism, or (ii) a radially extending formation which extends at least partially around an outer surface of the body. The at least one air escape passage may be positioned on a side of the formation that faces away from the outlet of the valve body. As mentioned hereinbefore, the one or more apertures or slots defined within the radially extending formation may have one or more flexible flap members applied externally thereto which serve to occlude the apertures or slots during inhalation, and open to allow exhaled air to pass through the apertures and past the flexible flap members, to the outside environment.

The outlet passage may provide unimpeded air and/or aerosolised drug flow between the chamber and the ambient environment or, during use, a user's mouth.

In one embodiment of the invention, the body may be in the form of a T-shaped connector comprising a downwardly extending conduit to which the bag may be attached and from which it may depend, the downwardly extending conduit being in fluid flow connection with a cross-pipe, the cross-pipe having an inlet for connecting to a medication cup, and an outlet defining an exit passage.

In another, preferred, embodiment of the invention, the body is in the form of a generally V-shaped mounting having. The V-shaped mounting may be formed by the opposing inlet passage and the outlet passage intersecting at an angle along their respective longitudinal axes where the angle creating the V defines an arc of preferably between 30 and 170 degrees, preferably 60 to 120 degrees, most preferably 90 degrees. The inlet and outlet passages may be cone-shaped. The perimeter of the inlet may be round, oval, elliptical, or irregular in shape. The V-shaped mounting may include a V-shaped interior surface, and may have a lower perimeter formed by the merging of the inferior and lateral aspects of the merging inlet and outlet ports that is generally oval in shape. This perimeter may constitute the portion of the mounting that receives the demountable bag. The interior of the V-shaped mounting is shaped and dimensioned to define a cavity that provides a passage for flow of air and/or medication between the inlet and the bag and between the bag and the mouthpiece. The interior of the V-shaped cavity may be sized and dimensioned to receive the bag, when the bag is folded into the cavity for portability purposes.

The inlet and outlet passages may be of roughly equal proportion in size, length, volume, diameter, or shape. The inlet and outlet may, in another embodiment, not be proportional in size, length, volume, diameter and/or shape.

The ratio of the major and minor axes of the oval perimeter in this embodiment may be between 1.01:1 and 6:1, preferably between 1.2:1 and 2:1, most preferably 1.38.

The outlet may be configured to be received by a user's mouth, either directly, or through a face mask. The inlet may be configured, as before, to receive a medication cup or exit port of a medication cup.

The invention extends in a further aspect thereof to a bag for a spacer device of the invention, wherein the bag has an opening including a collar that is shaped and dimensioned to fit securely to the lower perimeter of the body of the spacer device of the invention, thereby to releasably attach the bag to the body of the spacer device. The collar may extend along an upper periphery of the bag opening, and may extend at least partially around the opening of the bag. The bag opening may be biased towards an open, distended position by way of being made of a resiliently flexible material. The bag when ready for use, may spontaneously adopt a shape of an open inflated/distended position. This may occur through shape or material memory. The bag may be provided with a peripherally extending, resiliently flexible seam. The resiliently flexible seam serves to resist vertical collapse of the bag during inhalation and exhalation.

The capacity for the bag to adopt this shape may be engineered to ensure that negligible resistance to the collapse of the bag during inhalation is present. The collar may be made of a resiliently flexible material that urges the collar (and hence bag) against an inner surface of the mounting, in one embodiment. In another embodiment, the collar may be shaped and dimensioned to encircle and attach in a friction-fit—including an O-ring conformation—or snap-fit manner to the lower perimeter of the body. The bag may also be provided with a threaded collar that engages with a complementarily threaded portion of the lower perimeter of the body.

It is to be understood that the spacer device may include bags of many different sizes and shapes, with the choice depending on a number of factors including, but not limited to: the lung volume and inhalation capabilities of the user; the medical needs at the time of use; and the user preference (which may include merchandising choices) or to minimize awkwardness and conspicuousness when used in social settings.

BRIEF DESCRIPTION OF THE DRAWINGS

The description will be made with reference to the accompanying drawings in which.

DETAILED DESCRIPTION OF EMBODIMENTS

Figure 1:
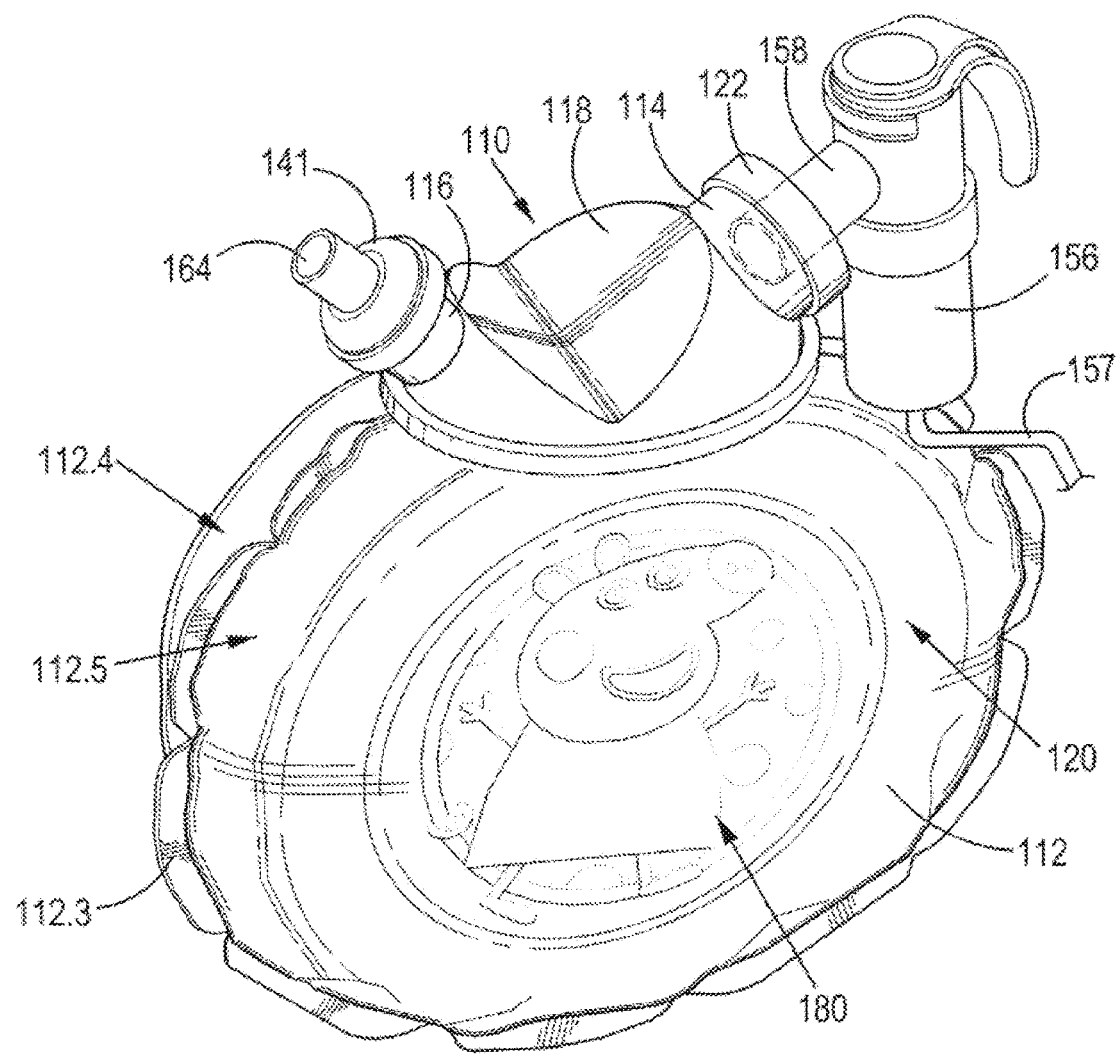
FIG. 1 is a front 3-D view of a spacer device for an inhaler according to a first embodiment of the invention, in use.
Figure 2A:
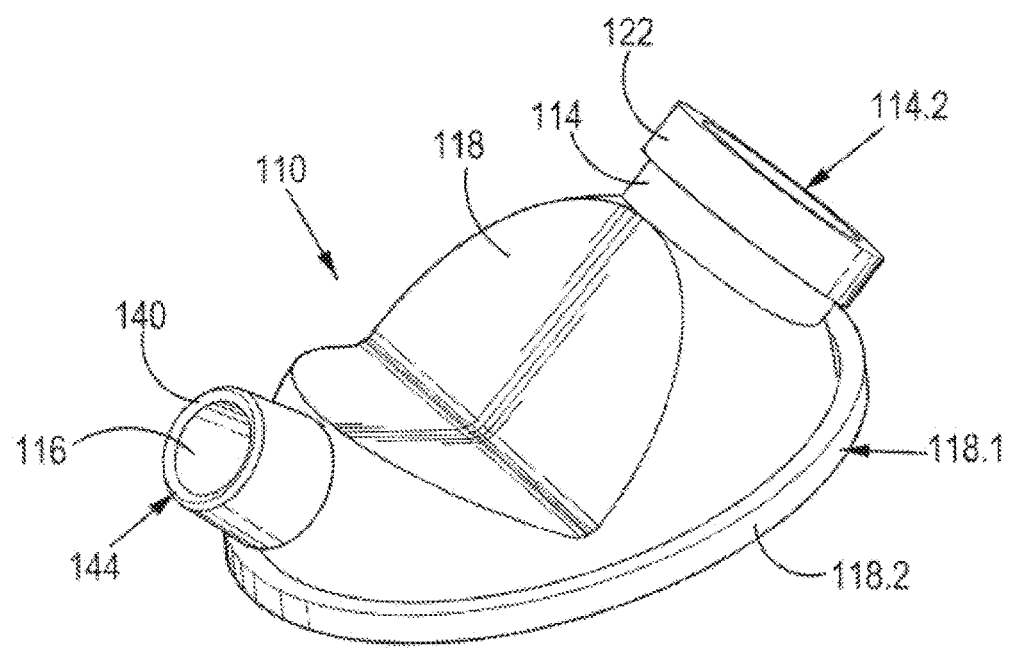
FIG. 2A is a front perspective view of the V-shaped body of spacer device shown in FIG. 1, shown by itself.
Figure 2B:
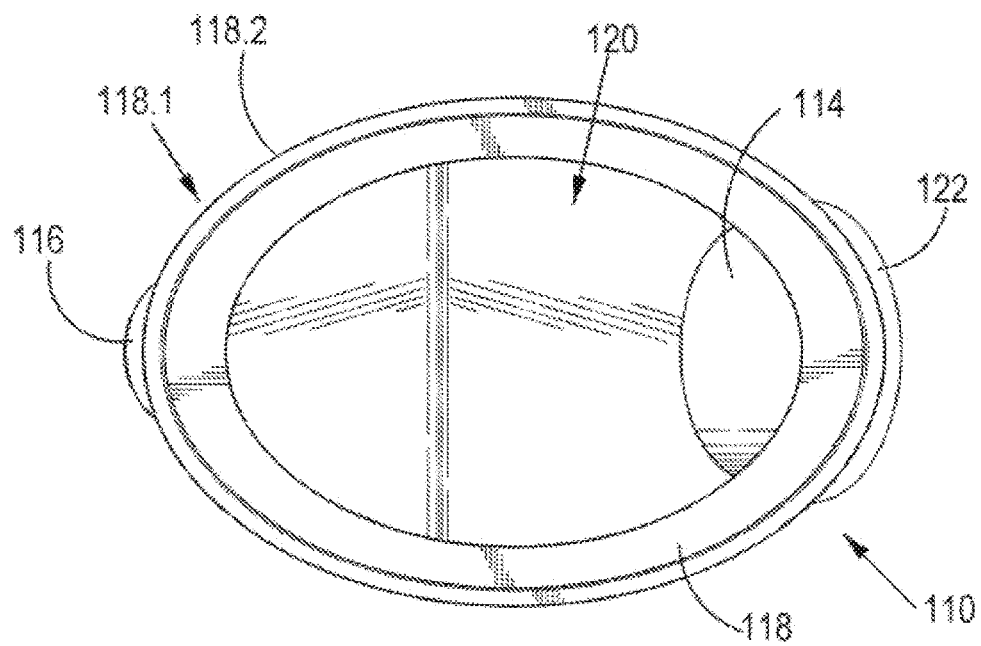
FIG. 2B is a bottom plan view of the V-shaped body of the spacer device shown in FIG. 1, shown by itself.
Figure 3:
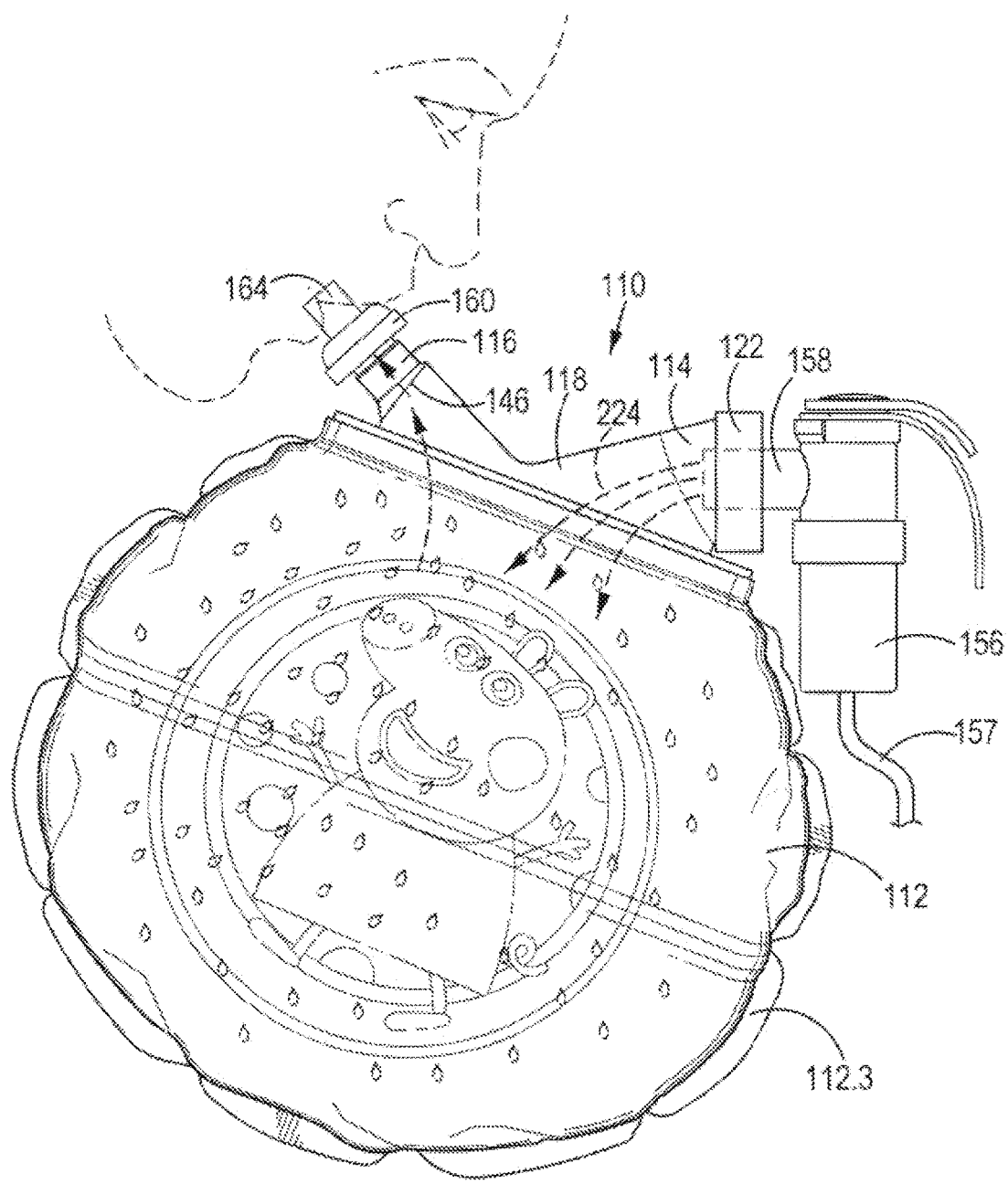
FIG. 3 is a partial cross-sectional side view of the first embodiment of the spacer device of the invention wherein the body is in the form of a V-shaped mounting.

Further features of the present invention are more fully described in the following description of several non-limiting embodiments thereof. This description is included solely for the purposes of exemplifying the present invention to the skilled addressee. It should not be understood as a restriction on the broad summary, disclosure or description of the invention as set out above. In the figures, incorporated to illustrate features of the example embodiment or embodiments, like reference numerals are used to identify like parts throughout.

The invention as described in by way of non-limiting example with reference to the drawings provides a spacer device for facilitating inhalation of medication delivered from an inhaler delivery device (such as a nebuliser).

In general, the spacer device of the invention includes a flexible, collapsible bag shaped and dimensioned to serve as reservoir for receiving a drug to be inhaled in a mist or cloud form from a nebuliser device, and a body (also referred to herein as a "base" in certain embodiments) with an inlet, or entrance, through which medication is discharged from a nebuliser device into the bag, and an outlet, or exit (which may include a valve, as described below, forming a mouthpiece through which the contents of the bag can be inhaled with the bag collapsing under the negative pressure created by the inhalation thereby promoting the emptying of all its contents into the mouth of the user and maximising the delivery of medication to the lungs of even unsophisticated users.

The valves in the mouthpiece control both the flow of aerosol from the bag into the user's mouth during inhalation, and the flow of exhaled air from the user's mouth to the outside during exhalation. This, combined with the flexible chamber, provides the spacer device with its unique functionality by forming a closed circuit, collapsible, reservoir system that eliminates wastage of aerosol during exhalation. By doing this, it ensures that 100% of the dose emitted by the nebuliser is delivered to the user's mouth—effectively doubling the dose delivered by standard nebulisers (which do not have this capacity) as well as eliminating environmental contamination concerns relating to the escaped aerosolised drug. The spacer device also provides the user with the freedom to use whatever breathing pattern the user prefers or is capable of at the time without impacting on the amount of the dose delivered to the lung. For instance, breathing can be slow and deep by a capable user, or by an unsophisticated user by way of regular, tidal breathing. Either way, 100% of the dose is delivered to the user's mouth. The angles of the inlet and outlet of the spacer device and the shape of the bag are designed to minimize impaction of drug particles therein or thereupon, thereby promoting laminar flow into and out of the bag and ports, and maximise emptying of the chamber.

Usefully, the size of the bag can be swapped to suit a user's needs—age, physical size, lung capacity, strength of inspiration, social awkwardness—and it has been found that a bag as small as 500 cm3 and as large as 1500 cm3 can achieve similar levels of drug particles being inhaled successfully, depending on the factors named above.

A pressurizable drug delivery device containing a pump for generating pressurized air or oxygen, generally referred to herein as a nebuliser, is attached to the inlet of the spacer invention device. This inlet can be modified to receive most common nebuliser outlets or a custom-made nebuliser can be built into the inlet.

With the nebuliser pump running, aerosolised droplets will continuously flow into the bag (reservoir), tending to fill it. Attached to the outlet of the current invention device is a valved mouthpiece that, during inhalation by a user, allows droplets from within the bag to flow into the mouth of the user. During exhalation, the valve closes and the exhaled air is diverted to the outside environment through openings situated around the periphery of the valve, or alternatively in another embodiment, through a simple flap valve situated on the upper surface of the mouthpiece. During the next inspiration, the flap valve or external openings close again by means of a small thin flap valve attached to the exterior wall along one side of each of the openings. At the same time, the internal flap valves open once again, and the next load of aerosolised droplets, which in the meantime had been continuously produced by the nebuliser and accumulating in the bag, can now be inhaled from the bag into the user's mouth.

This all means that at no stage during breathing (inhalation or exhalation), are aerosolized droplets produced by the nebuliser pump allowed to escape to the exterior environment. These droplets are therefore trapped in a closed-circuit system where are the only possible escape is into the user's mouth on their way to the lungs during inhalation.

To avoid over- or under-supply, the amount of aerosolised droplets leaving the device can be controlled in a number of ways to suit the needs of the user. Firstly, the flow of compressed air into the nebuliser may be adjustable within certain limits. Another option is that the bags on the device can be changed to find a suitable size and volume which suits the user and will enable the user to breath comfortably without having to adjust their breathing pattern if they are not capable. Many users, however, would be capable and willing to produce a breathing manoeuvre that will favour enhancement of the amount of inhaled drug delivered to the long, then this could be implemented as well. An example of this is slow deep inhalations which flavour the increased delivery to the lungs as well as more peripheral and even distribution of particles in the lung. All of this is particularly important for unsophisticated or compromised users such as the young or elderly, or those who are unwell.

Referring to the drawings, reference numeral 110 refers generally to a spacer device according to one embodiment of the invention, shown in FIGS. 1 to 5, while reference numeral 210 refers generally to a spacer device according to a second embodiment of the invention shown in the remainder of the drawings.

Referring to FIG. 1, in one preferred embodiment of the invention, there is shown a spacer device 110 comprising a metallised, anti-static or low-static bag 112 of low, or no, distensibility attached to a body 118. The bag 112 is made of an electrically conductive material, such as a metal or aluminium foil. In one embodiment the bag 112 is made of a metallised film or metallised biaxially-oriented polyethylene terephthalate (BoPET) or another similar flexible polymer, typically Mylar®. Alternatively, the bag 112 can be treated with an antistatic agent forming a static dissipative coating or layer on the bag 112. The same applies to the body 118, which can be made from, laminated to, or coated with, an anti-static coating or layer. The body 118 is typically made from a metal such as aluminium in this embodiment (although not restricted to this) or a metallised compound (such as metallised plastic, although not restricted to this), or a metal-coated compound such as a high-density plastics material (although not restricted to this) in other embodiments.

The body 118 includes inlet 114 and opposed outlet 116, the inlet 114 and opposed outlet 116 being provided on, and integral with, the body 118. The body 118 and bag 112 combine to form chamber 120 for receiving aerosolised medication.

The inlet 114 and outlet 116 each are in the form of a port that is in fluid flow communication with the chamber 120. The inlet 114 and outlet 116 define, and are separated by, a broad V-formation formed as part of the body 118. The body 118 further includes an elliptical lower perimeter 118.1 defining flange 118.2, for demountably receiving bag 112.

Figure 4A:
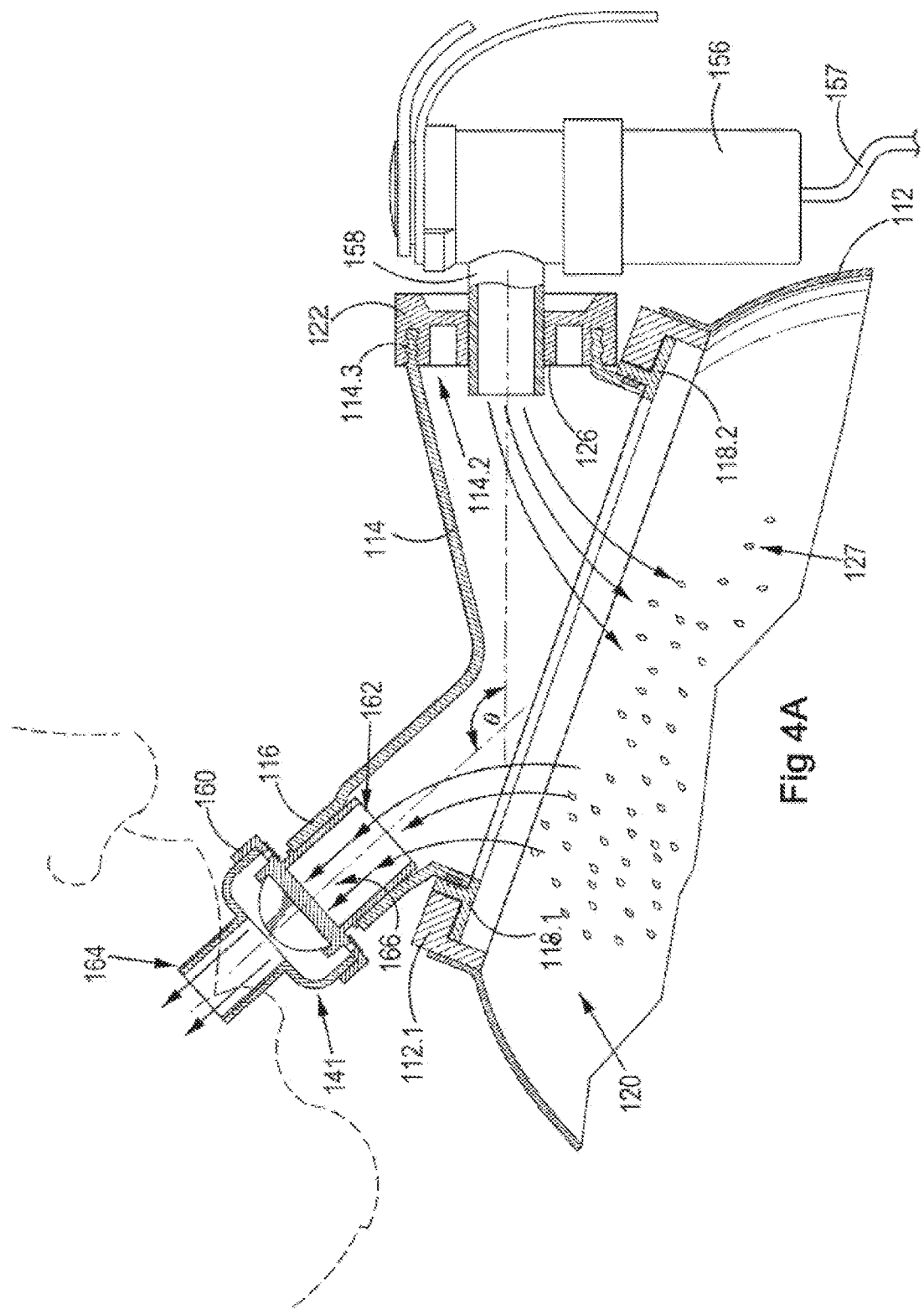
FIG. 4A is a cross-sectional view of the embodiment shown in FIG. 1, showing the formation of droplets in the formation of a cloud or mist in the cavity defined between the body and the bag, and when inhaled by a user.
Figure 4B:
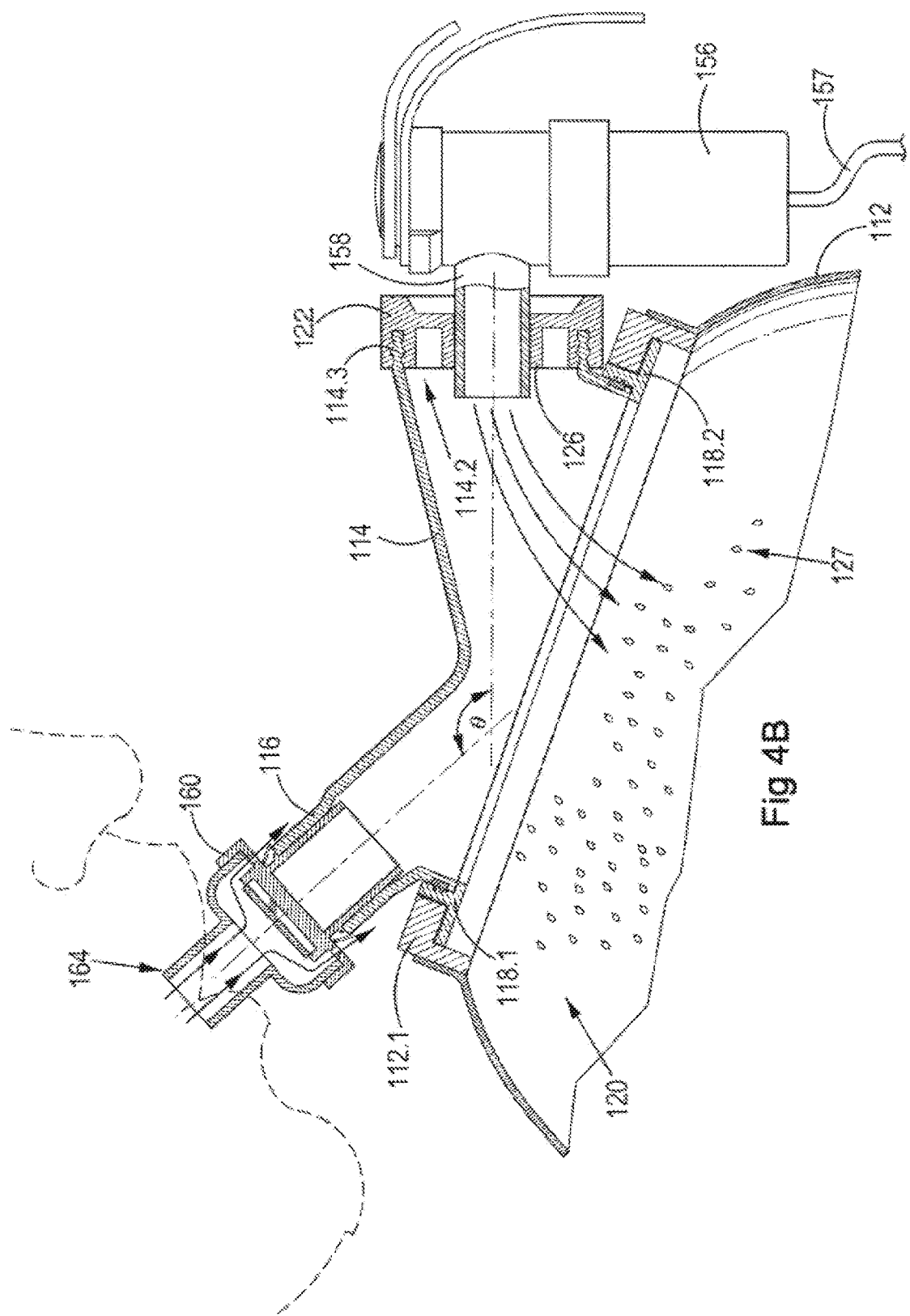
FIG. 4B is a further cross-sectional view of the embodiment of the invention shown in FIGS. 1 ad 4A, when in use, during exhalation.
Figure 5:
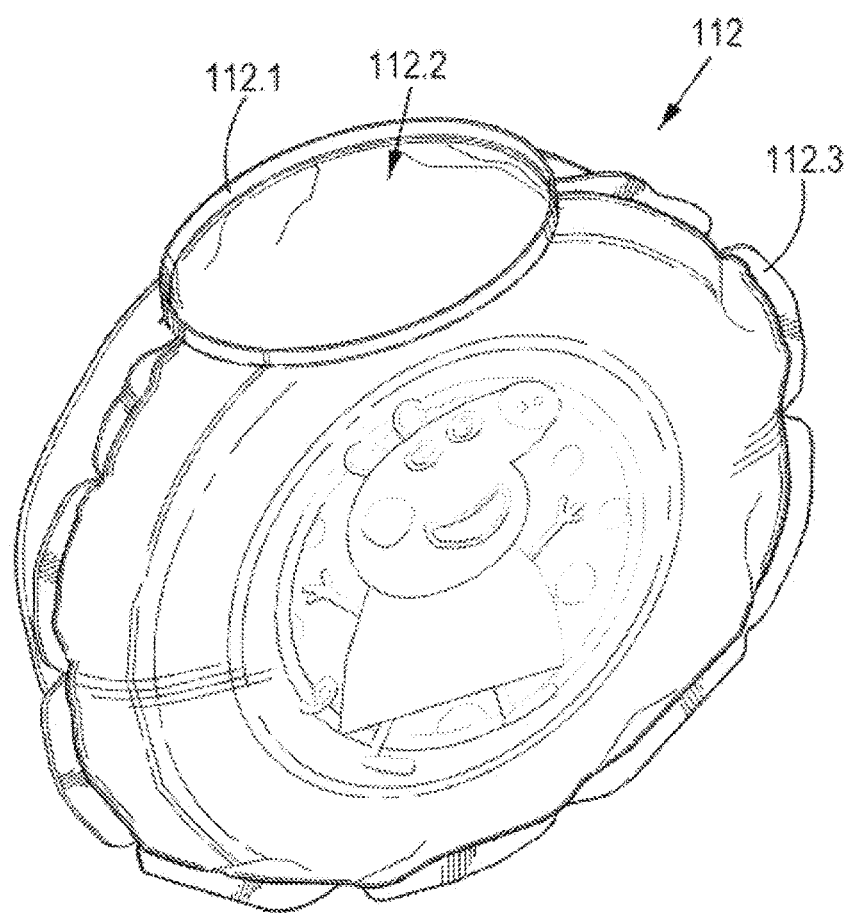
FIG. 5 is a 3-D view of a bag in accordance with one aspect of the invention, for use with the spacer device of the invention.
Figure 6:
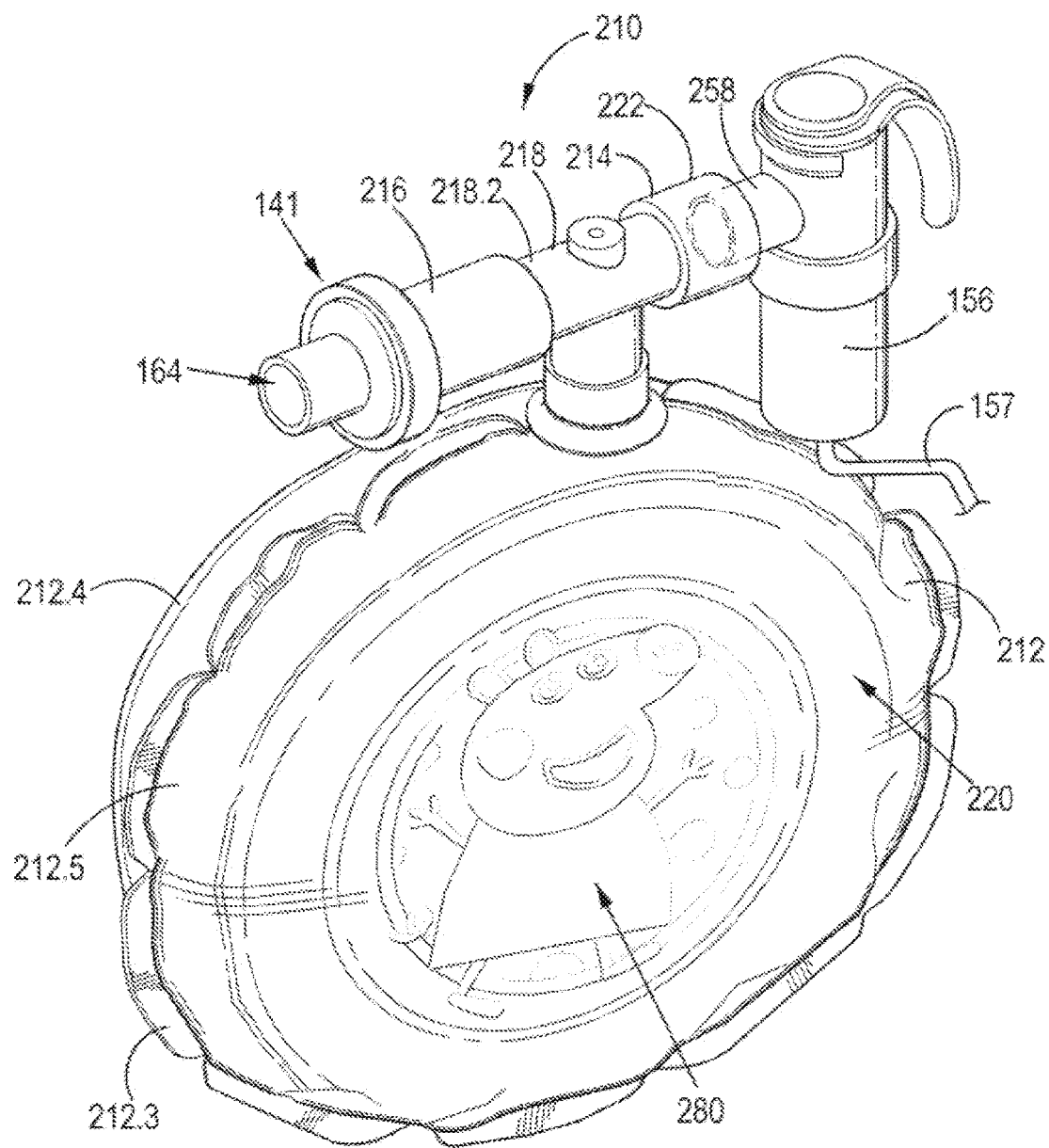
FIG. 6 is a 3-D view of a second embodiment of the spacer device of the invention.

As may best be seen in FIGS. 4A, 4B, and 5, the bag 112 includes a connecting formation in the form of an elasticated, peripherally co-extensive rib 112.1 attached to an opening 112.2 (best seen in FIG. 19) defined within an operatively upper section of the bag 112. The rib 112.1 attaches to the flange 118.2 to provide an effective seal between the bag 112 and the body 118. FIG. 19 also provides an indication of how the bag 12 may look prior to being fully inflated.

In another embodiment (not illustrated), the bag 112 opening 112.2 (and hence rib 112.1) is received over—and thus covers—the flange 118.2, the bag 112 having a constrictive elastic rib or O-ring 112.1 that can provide an effective seal between the bag 112 and the flange 118.2.

The embodiment shown in FIGS. 4A and 4B shows that the flange 118.2 can be threadedly mounted to the body 118 using thread formations 118.3 to facilitate cleaning or autoclaving of the body 118. In other embodiments shown in FIGS. 11, 14, and 17, the flange 118.2 is formed integrally with the body 118, or can be clipped in place.

Returning to FIG. 1, the inlet 114 includes an annular connector 122 for receiving a mouthpiece 158 of a medication cup ("pot") 156 of a nebuliser (not shown, but connected upstream from medication cup 156 and in fluid flow connection therewith via conduit 157), the medication cup 156 being connected in fluid flow fashion to the inlet 114, thereby allowing direct communication between the nebuliser medication 156 and the chamber 120 to allow for generally unimpeded cloud formation within the chamber 120 when a drug contained within medication cup 156 is dispersed into chamber 120 by the nebuliser. The annular connector 122 is screwed or clipped on to an end 114.2 of the inlet 114 using threads or interference fittings 114.3 (best seen in FIG. 4B) provided proximal said end 114.2. It is to be understood that the annular connector 122 can also be connected to the inlet 114 in a snap fit or friction fit manner (not shown). The annular connector 122 includes a sealing collar 126 in the form of a resiliently flexible inner annulus for sealingly receiving the mouthpiece 158.

As may best be seen in FIGS. 2A and 2B, and as mentioned hereinbefore, the body 118 has the inlet 114 and outlet 116 ports integrally formed therein, in unitary construction, such that the longitudinal axes 114.1, 116.1 of the inlet and outlet ports (shown in FIGS. 4A and 4B), respectively, when intersected, define an arc having an angle (shown as Θ) of between 30 degrees and 170 degrees. The V-shape defined by the inlet 114 and outlet 116 ports has a general angle of 90 degrees which corresponds generally to angle (Θ) which is similarly approximately 90 degrees in the embodiment shown in FIGS. 4A and 4B.

As shown in FIG. 3, this configuration assists in ensuring that the inhalant drug (shown as microdispersion droplets 127) is guided into and fully enters the chamber 120 first rather than being passed directly through between inlet 114 and outlet 116 as would have been the case if inlet 114 and outlet 116 had been in register, i.e. when the angle (Θ) would have been 180 degrees or thereabouts.

In this way, the inhalant droplets 127 enter the chamber 120 in a smooth fluid flow manner without depositing either on internal structures to any great extent, nor being expelled directly into the oral cavity or throat of the user by shooting directly through outlet 116. The chamber 120 thus serves as reservoir for the inhalant drug and facilitates vapour or cloud formation within the chamber 120, from where the inhalant droplets 127 can be inhaled at a tempo and velocity that the user is comfortable with, without significant loss of inhalant drug to the atmosphere or external environment. The angle of the inlet 114 and outlet 116, combined with the smooth, unimpeded entry of the inhalant droplets 127 into the chamber 120, allow for a much higher percentage of the active drug to be inhaled by a user through outlet 116 than would have been the case without such an arrangement. Mouthpiece 140 has a proximal end 144 (best seen in FIG. 2A) and a distal end 146 (best seen in FIG. 3). The mouthpiece 140 is flared towards its proximal end 144 such that the outlet passage 142 is wider at its opening into the chamber 120 and narrower at the distal end 146 leading to the environment, or to the user's mouth in use either directly or through a valve (see description of valve below). Thus in use, the mouthpiece 140 is shaped to funnel the airflow and drug from the chamber 120.

Furthermore, the provision of the bag 112 on the operative underside of (i.e. depending downwardly from) the body 118 ensures that the bag 112 does not impede visual referencing of the inhaler device 156 by the user during use (see FIG. 3), leading also to more accurate, yet less intrusive, use of the device 110 by the user.

As may be seen in FIGS. 2B, 4A and 4B, the interior of the body 118 is V-shaped, commensurate with the outside of the body 118. Testing has shown that the possibility of the interior of the body 118 being occluded by the bag 112 during sharp inhalation is slight to non-existent. For portability purposes, however, the bag 112 may be nearly completely received or folded within the interior of the body 118. This serves to decrease the size and conspicuousness of the device 110, making it easy to fit the device 110 into a purse, handbag, or carry bag.

In use, the bag 112 decreases in size very slightly in vertical cross-section during inhalation, especially given the fact that it is under constant pressure from the nebuliser, and generally the bag maintains its vertical dimensions due to the flexible resilience of seam 112.3 forming part of the bag 112. Inhalation thus generally results preferentially in the two opposing sides or "cheeks" 112.4, 112.5 of the bag 112 being drawn closer to each other during inhalation, rather than the bag 112 being sucked into, and collapsing inwardly into, the inner cavity of the body 118 during sharp inhalation. The Applicant has found that the configuration and shape of the bag 112, especially the shape-memory seam 112.3, prevents this from happening, even with sharp inhalation.

Advantageously, a smaller bag may be used for children, the elderly, or those with compromised lung function (or to avoid conspicuousness), while larger bags may be used for adults. Smaller bags may also be more functional with low flow nebulisers, such as vibrating mesh nebulisers, or the like.

The longitudinal axis (major axis) of the oval perimeter 118.1 in this embodiment is 9 cm. In another embodiment, this may be less (down to 2 cm, or less), or more (up to 20 cm, or more). The axis defining the maximum width (minor axis) of the oval perimeter 118.1 in this embodiment is 6.5 cm. In another embodiment, this may be less (down to 1 cm, or less) or more (up to 15 cm, or more). The ratio between the major axis and minor axis is typically 1.38:1.

The thickness of the wall of the V-shaped mounting can be adjusted for considerations relating to weight, strength, feel, and construction. In this embodiment, the wall is 2 mm thick through most of the mounting although this may vary. In other embodiments, this may be less, (down to 1 mm, or less) or more (up to 8 mm, or more).

As shown in FIGS. 1, 3, 4A to 6, a key feature contributing to the functional characteristics of the invention is the use made of a valve 141 attached to outlet 216 which serves to allow for the inhalation of aerosolised drug particles 227 through passage 246, while preventing the entry of exhaled air from a user into chamber 220. The valve 141 comprises a body 160 including an inlet 162 through which medication from a nebuliser (via spacer device 110) is received, an outlet 164 which exits to the atmosphere, a passageway 166

(shown in FIG. 4A and FIGS. 11A-D) connecting the inlet and outlet, and at least one selectively activatable occlusion member interspersed between the inlet 162 and outlet 164 that prevents the flow or entrainment of exhaled air back into the spacer device from the outlet when the pressure of the exhaled air entering the outlet 164 exceeds the pressure of the air entering the inlet 162 of the valve 141 from the chamber 120. The body 160 comprises two shells 160.1, forming the inlet side, and 160.2, forming the outlet side, most clearly shown in FIGS. 11A to 11D. The two shells 160.1 and 160.2 connect medially in a click fit manner to form body 160.

Figure 11A:
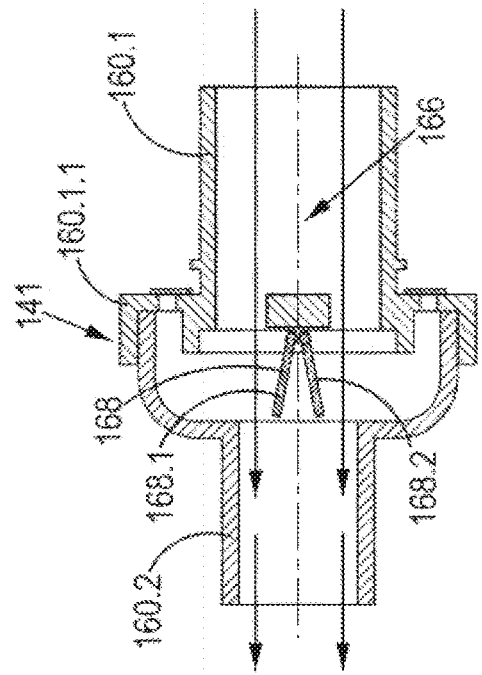
FIGS. 11A, 11B, 11C, and 11D are cross-sectional views of the valve shown in FIGS. 10A and 10B.
Figure 11B:
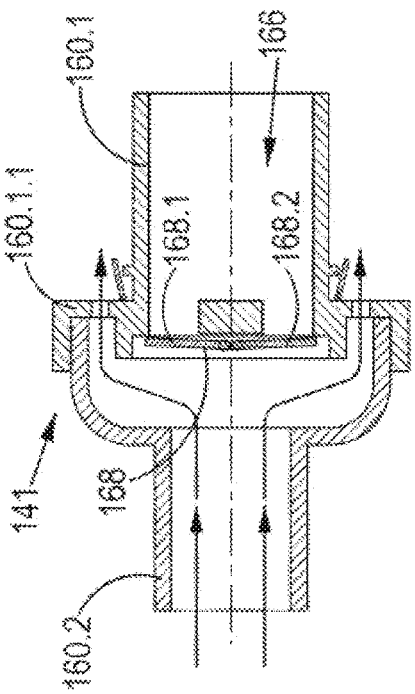
Figure 11C:
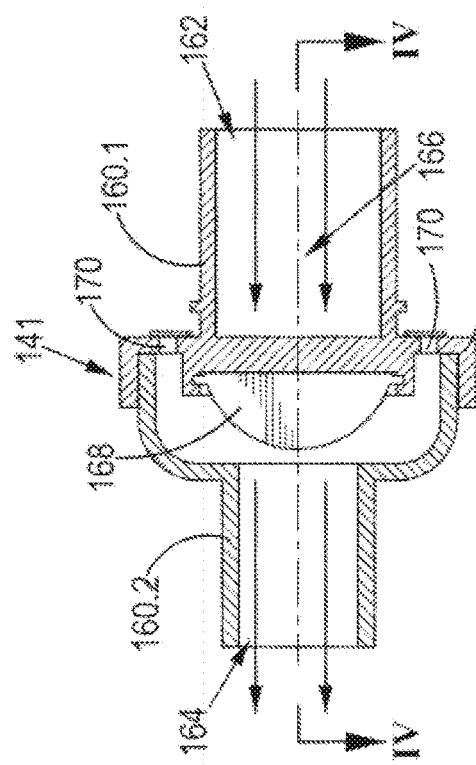
Figure 11D:
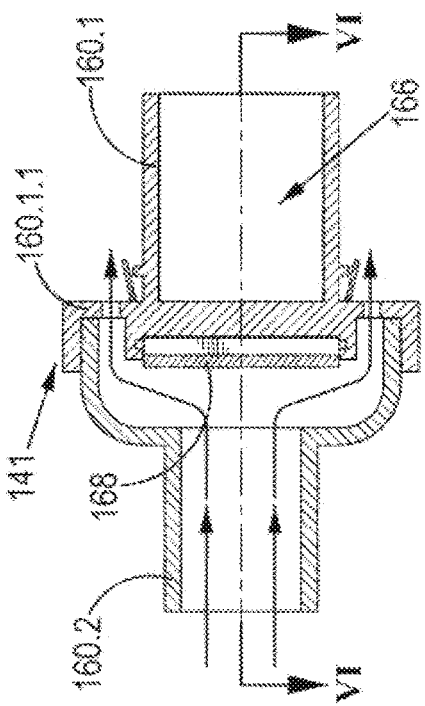

In one embodiment, the occlusion member is in the form of a flexible flap 168 of unitary construction, but which forms two wings 168.1, 168.2 (best seen in FIG. 11B) working in unison to occlude passageway 166. The, or each, wing 168.1, 168.2 is in the form of a soft, flexible filament which can readily bend or flex under pressure from the air emanating from the chamber 120, but which is flexible enough to close when a slight overpressure is inflicted thereupon by exhaled air entering the passageway through outlet 164. In the embodiment shown, it is made of a soft rubberised plastic which provides a secure seal when the flaps are in the occluded position, as shown in FIGS. 11C and 11D.

The, or each flap, may be attached to the body 160 of the valve 141. Alternatively, the, or each, wing 168.1, 168.2 of the flap 168 is attached to a central spine 160.1 which is formed integrally with shell 160.1 and serves to bifurcate the passageway defined between the inlet 162 and outlet 164 of the valve body 160.

Figure 10A:
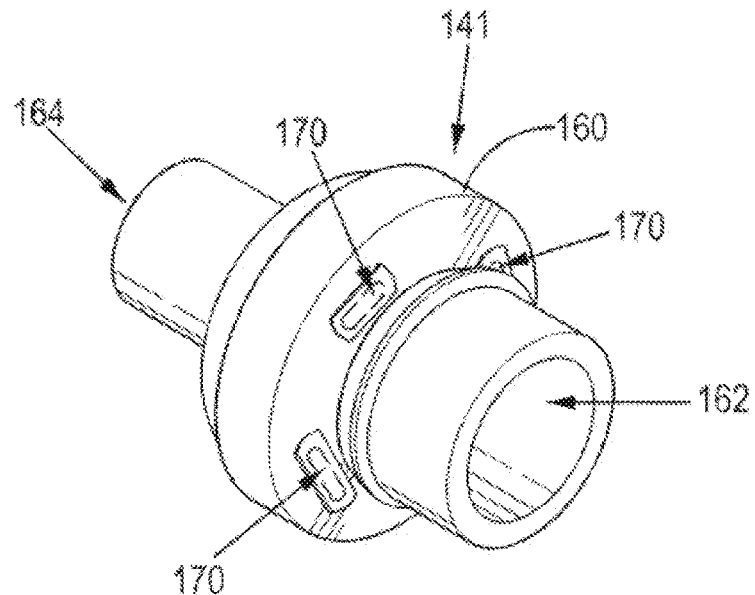
FIGS. 10A and 10B show a rear 3-D and side view of a valve of the invention.
Figure 10B:
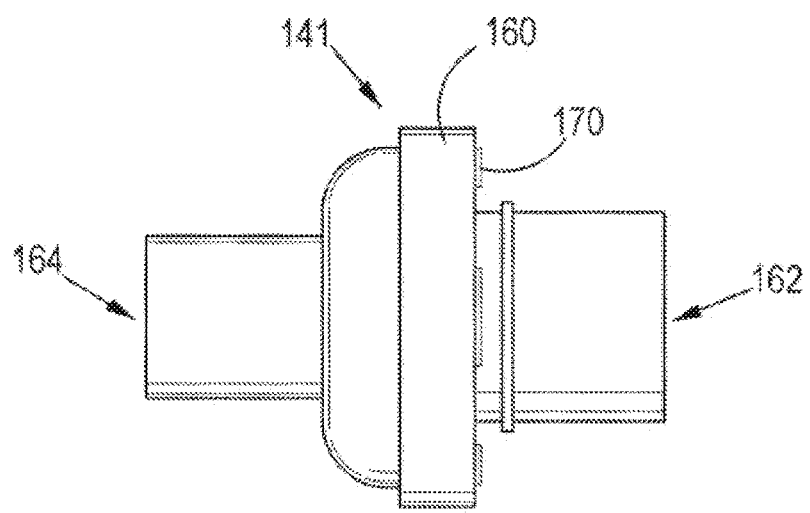

The valve body 160 further includes escape passages, which in one embodiment, may be in the form of slots 170 (best seen in FIGS. 10A and 10B) defined within an annular peripherally extending formation in the form of a collar 160.1.1 formed integrally with shell 160.1 for the escape of air upon occlusion of the passageway of the body 160 by the occlusion member 168, i.e. upon activation of the occlusion member 168 when, for example, a user forcefully exhales into a mouthpiece or facemask attached to the outlet of the valve body at a pressure which exceeds that of aerosol or air being voided from the nebuliser.

The slots 170 are defined within the shell 160.1 of body 160 that allows for the exit of air. The slots 170 are configured to exit from the valve body 160 in a direction away from the outlet 164 of the valve body 160, in other words away from the face of a user that may be exhaling into outlet 164 (or a mouthpiece formed by the outlet) of the valve body 160. The size, shape, number, and dimension of the slots can be chosen to accommodate flow rates of medication, breathing frequency, exhalation force, and the like, to minimize the effects of exhalation and to encourage rebreathing of medication contained within the bag.

Advantageously, in one embodiment of the invention, best seen in FIGS. 10A, 18B, and 11A to 11D, the one or more slots 170 defined within the radially extending formation each have a flexible flap member 172 associated therewith. The flap members 172 serve to occlude the slots 170 during inhalation, and open to allow exhaled air to pass through the apertures 170 and past the flexible flap members 172, to the exterior environment, away from a user's face. In another embodiment, the escape valve, instead of the radially placed apertures, is in the form of a simple flap valve located on the upper surface of the mouthpiece and has exactly the same functionality.

The above described arrangement means that at no stage during breathing (inhalation or exhalation) are any aerosolized or microdispersion droplets, produced by the nebuliser pump, allowed to escape to the exterior environment. These droplets are therefore trapped in a closed-circuit system where the only escape is into the user's oral cavity, on their way to the lungs during inhalation.

In the embodiment shown in FIGS. 6 to 9, this embodiment of the spacer device 110 of the invention allows the body 118 to be shortened to a desired length to suit the function and handling capability of the spacer device 110. This embodiment allows the chamber formed by bag 112 and body 118, by inflating and deflating below the body 118, to be less intrusive to the user.

Usefully, the body (or "base") 118 and the bag 112—together defining chamber 120—can be separable allowing the bag 112 to be disconnected from the body 112. Amongst other indications, this disconnection may be indicated when a bag 112 is required to be cleaned or replaced when worn or contaminated, or simply replaced with one of a different size (volume) bag 112 depending on the need and capabilities of the user.

The bag 112, when ready for use, spontaneously adopts a fully inflated position filled with air. The bag 112 is made of soft material providing no or very little resistance to expansion and collapse making it capable of full deflation and re-inflation while the user inhales and exhales during rebreathing. As mentioned hereinbefore, the bag 112 is metallised (typically made from a thin-section, easily collapsible polymeric metallised film such as Mylar®) such that it conducts electricity and therefore does not develop static electricity. The bag 112 can either collapse fully during inhalation allowing complete emptying of all the medication mist or droplets 127 originally expelled into the chamber 120 from the nebuliser/medication cup 156 in one breath, or collapse partially (depending on the user's breathing comfort and capabilities).

In FIGS. 6 to 11D, there is shown a spacer device 210 in accordance with another embodiment of the invention for use with an inhalant drug delivery device (IDDD) such as a nebuliser or forced air device to assist with breathing and inhalation, the nebuliser being represented by way of medication cup 256 which contains drugs to be dispersed into a user' airways. The spacer device 210 comprises an inflatable bag 212 having an inlet 212.1 (similar to 112.1 shown in FIG. 5) attached to a T-shaped spacer body 218. The spacer body 218 includes a downwardly depending conduit 218.1 that is attached medially to, and in fluid flow connection with, a cross-pipe conduit 218.2 that also forms part of the body 218. The body 218 is generally of unitary construction to smooth the flow of air or aerosolised medication within the body 218 (i.e. to promote laminar flow), or is comprised of separate conduits attached to one another.

The bag 212 is in the form of a balloon that is roughly disc-shaped when deflated and roughly spherical when inflated (see FIG. 6). However, the bag 212 can have other shapes as desired, for example such as being ovoid, lenticular, frustoconical, or rugby-ball shaped when inflated, in other embodiments. As before, the bag 212 can include concertina-like folds so that during deflation the bag 212 is directed to collapse in a predetermined manner to enhance both the functioning thereof during deflation as well as to improve its aesthetics. The bag 212 can be non-symmetrical so that, for example, it has a larger inflated volume on an operative lower side thereof or vice versa.

As before, the bag 212 is in the form of a flexible, non-distensible bladder that, together with inlet 214 and outlet 216 define a body 218, the bag 212 and body 218 forming a chamber 220. In one embodiment the bag 212 is made of an electrically conductive material, such as metal or aluminium foil. In another embodiment the bag 212 is made of a metallised film or metallised biaxially-oriented polyethylene terephthalate (BoPET) or other similar flexible polymer, typically Mylar®. Alternatively, the bag 212 can be treated with an antistatic agent forming a static dissipative coating or layer on the bag 212. The same applies to the body 218, which can be made from, laminated to, or coated with, an anti-static coating or layer.

As with the first embodiment, the bag 212 is constructed with one or more seams 212.3 made of, or containing, a resiliently flexible or shape-memory material providing the bag with shape memory that opens the bag 212 in the inflated position when preparing it for use. The one or more seams 212.3 may also control the way the bag 212 deflates in a predetermined manner if necessary to enhance both the functioning thereof during deflation as well as to improve its aesthetics. The chamber 220 has a volume sufficiently large that the bag 212 should not be overinflated or fully deflated (collapsed) in normal use during breathing by a user. In this regard, the volume of the bag 212 can be selected dependent on the age of the user such that a smaller bag 212 is provided for a younger user, while a larger bag 212 is provided for a larger user.

The inlet 214 is in the form of a socket configured to receive an outlet from medication cup 256 ("pot") having mouthpiece 258, the medication cup 256 being downstream of a forced or pressurised air inhalant drug-delivery device (IDDD), such as a nebuliser (not shown). The medication cup 256 is connected via conduit 257 to the nebuliser.

Figure 7:
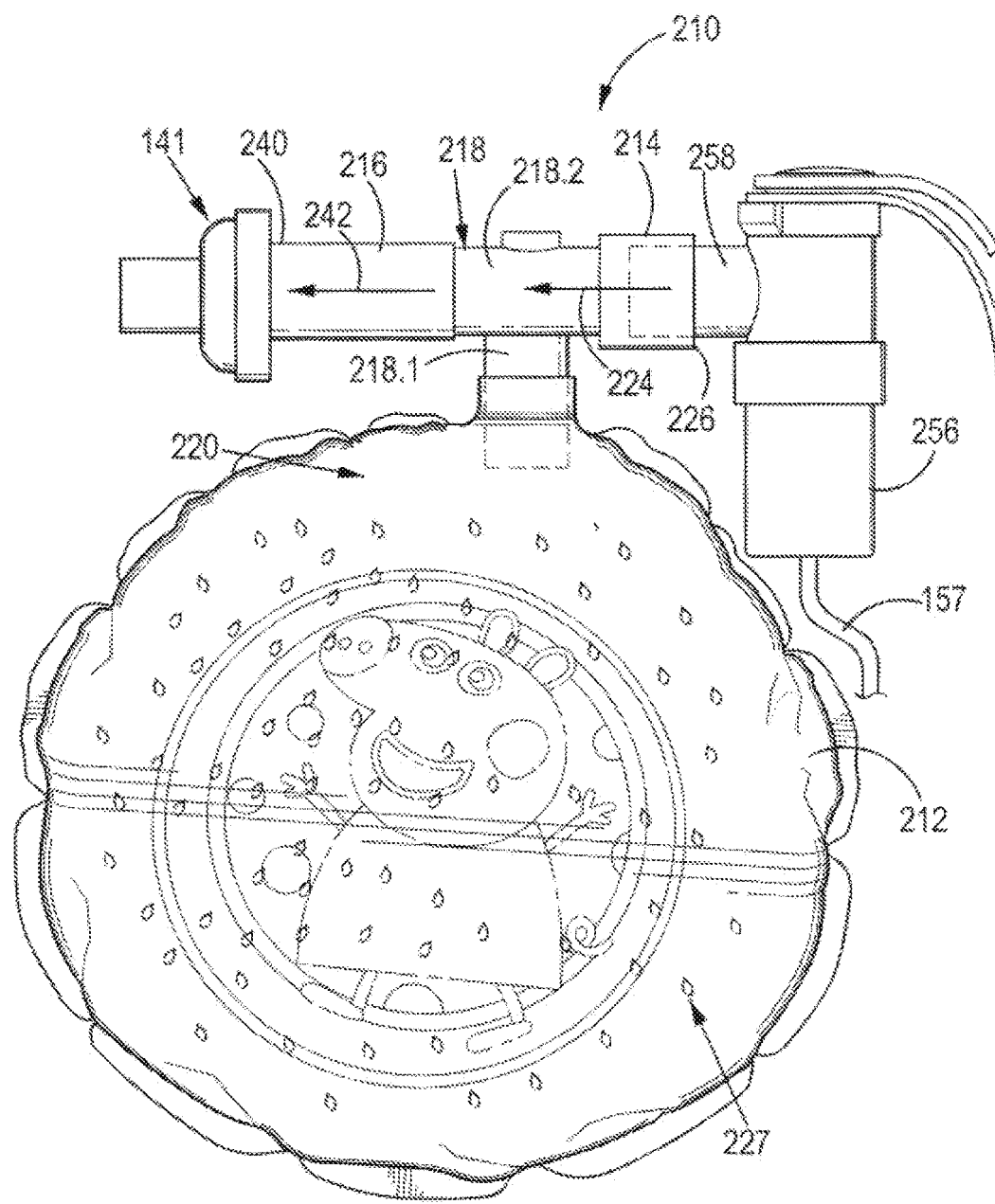
FIG. 7 is a part cross-sectional side of the second embodiment of the spacer device shown in FIG. 6.
Figure 8:
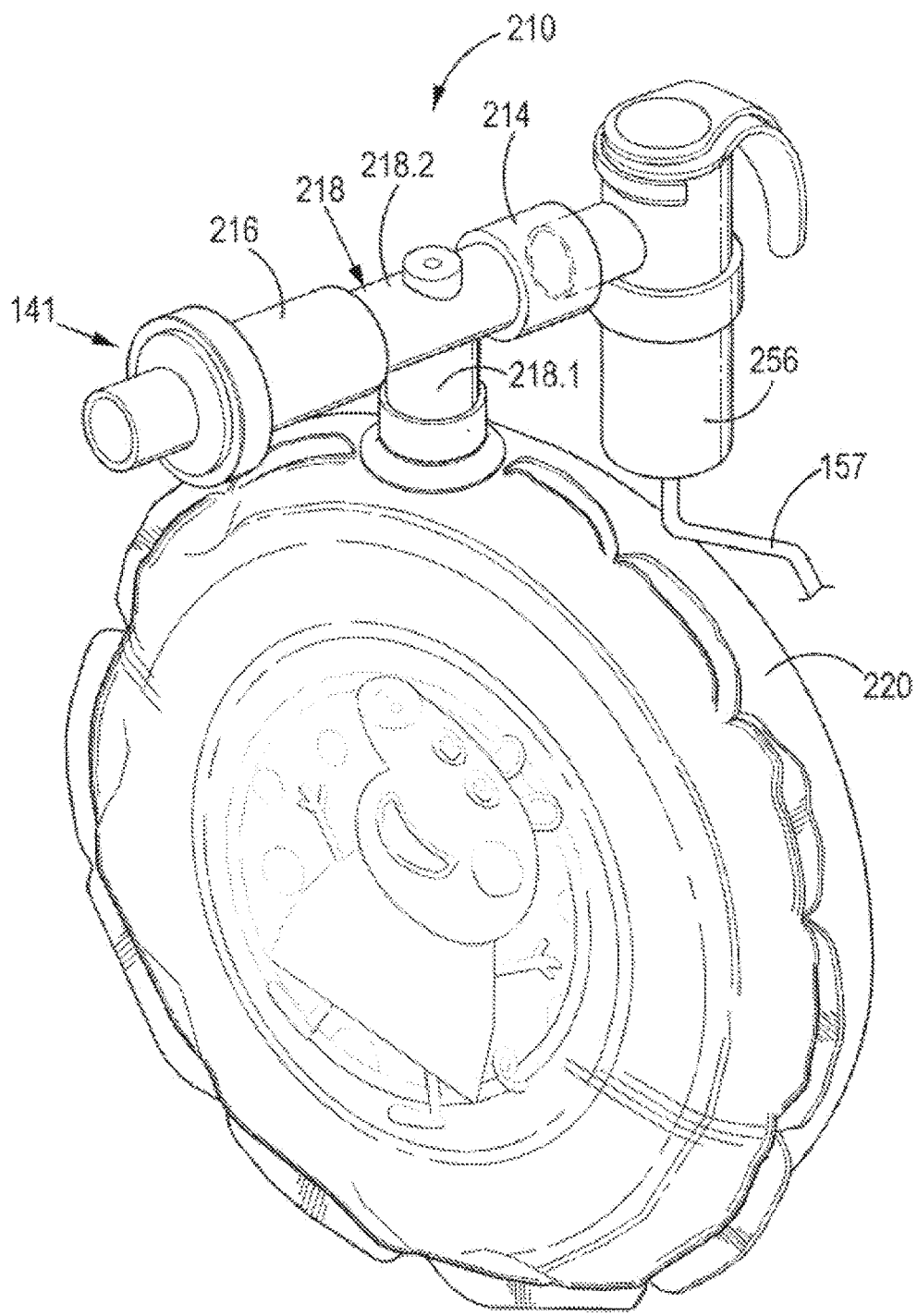
FIG. 8 is 3-D view of the second embodiment of the spacer device of the invention, wherein the bag is rotated by ninety degrees.
Figure 9:
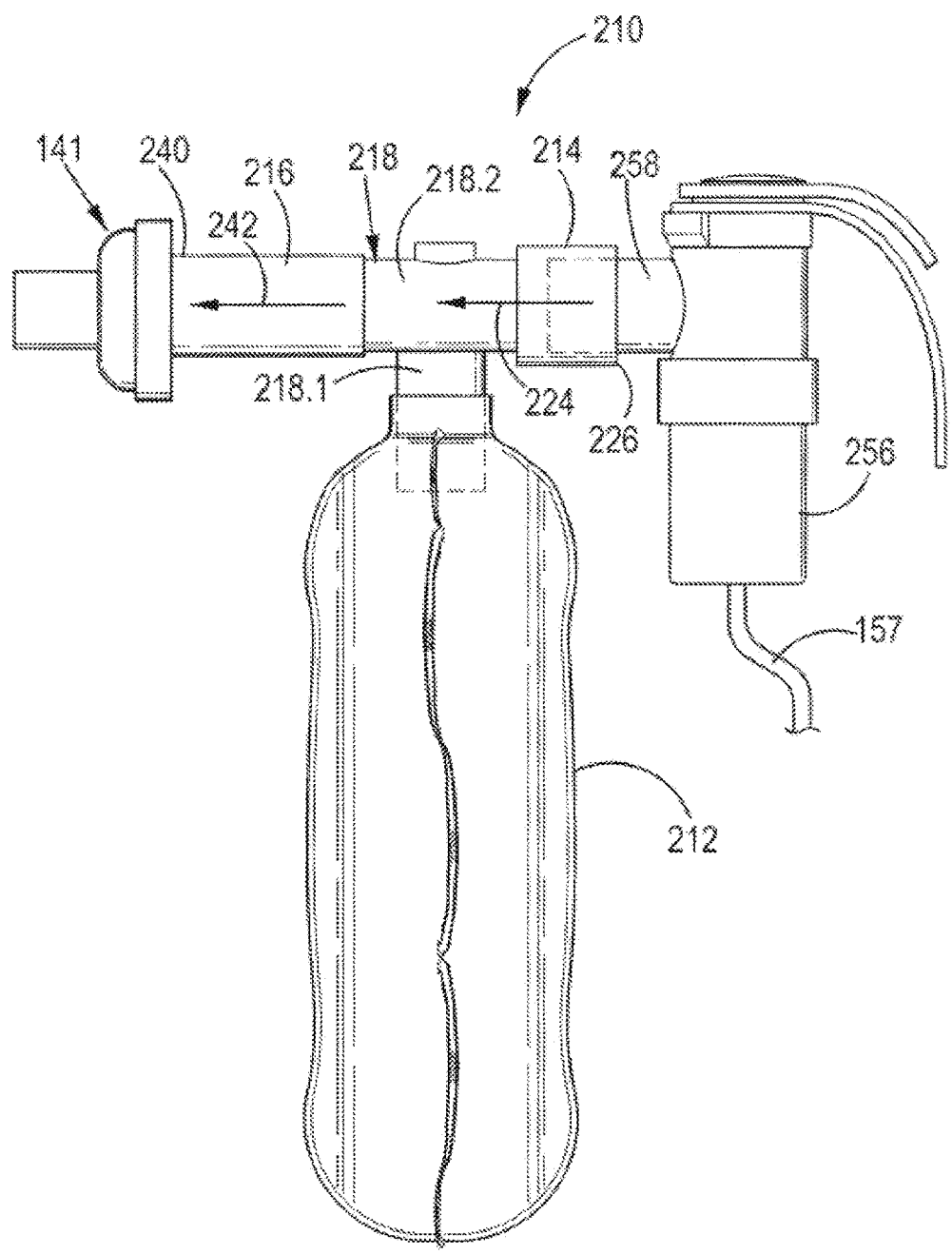
FIG. 9 is a side-view of the embodiment shown in FIG. 8.

The inlet 14 includes a mount 222 defining an inlet passage 224 defined by inlet 214 into the chamber 220, the inlet passage 224 best shown in FIG. 7. The mount 222 includes a sealing collar 226 attached to the mount 222 to surround the inlet passage 224 formed by inlet 214. The collar 226 is contoured so that the inlet passage 224 is substantially complementary to the shape of a mouthpiece. The collar 26 is also resiliently flexible so that it can cater for minor variations in the shape of the mouthpiece and conform in sealing contact therewith. When the mouthpiece 258 is attached to the inlet 214, mouthpiece 258 is pressed into the inlet passage 224 by press-fit so that the collar 226 annularly seals against mouthpiece 258.

In this embodiment, similar to the mount 122 of the first embodiment, the mount 222 comprises a substantially circular disc 130 with an annular skirt 132 depending from the disc 130 and leading to edge 134. The inlet passage 24 is circular in shape, although it may be shaped in other embodiments to be conformable to a wide range of nebuliser mouthpieces and may also be sold in kit form.

In other embodiments, the inlet passage 224 can be shaped to be substantially complimentary with the mouthpiece 258 with the collar 226 having a regular cross-section. For example, such a collar 226 could be shaped as a flexible torus with an outer groove so that it could be clipped over the edge of the disc 130 surrounding the inlet passage 224. Alternatively, the disc 130 can be made thicker and the collar 226 could be an O-ring held within a groove provided in the disc 130 within the inlet passage 224.

The mount 222 can optionally include a connector (not shown) arranged to be inserted into the inlet 14 to accommodate different types of nebulisers or medication cups 256. The mount 222, and connector if provided, is made of an electrically conductive material to avoid build-up of static electricity or, alternatively, is coated with an antistatic agent.

The outlet 216, in a certain embodiment, includes an integral mouthpiece 240 defining an outlet passage 242. In other embodiments, the outlet 16 is shaped to engage with an external mouthpiece that is connectable to the outlet 216. The mouthpiece 240 is substantially rigid so that it cannot be deformed or pressed closed. It is shaped and dimensioned to be able to receive valve 141. The mouthpiece 240 is ovoid, circular, lenticular, or elliptically shaped in its cross-section being transverse to the operative direction of the outlet passage 42, thereby being generally complementary in shape with a user's mouth so that is can be sealingly received in their mouth, or to sealingly engage with valve 141.

The outlet passage 242 is normally open so that the chamber 20 is in free communication with the ambient environment when the mouthpiece 240 is not sealingly held in a user's mouth, either directly or via a valve, such as valve 141. As such, the invention includes a valve 141 for preventing entry of exhaled air when a user exhales.

The following description applies to both embodiments 110 and 210 of the spacer device of the invention, even though mention is made of the second embodiment only in this description or sake of brevity. In use with a conventional IDDD such as a nebuliser, a user will initially attach their medication cup 256 to the spacer device 210, 220 by inserting the nozzle 258 from the nebuliser pot 256 into the inlet passage 224 so that the collar 226 seals around the nozzle 258. The nebuliser is switched on and pressurised air, gas or oxygen is passed through conduit 257, via medication cup 256 and 258, into chamber 220. The user then breathes in a normal manner with the exhaled breath being passed to the atmosphere via valve 141.

Once the bag 212 is inflated by way of the pressurised air containing the drug aerosol (microdispersion) 227, the user places their mouth over the valve 141 and inhales from the bag 212. Thereafter the user breathes in a normal cyclical manner—either with slow deep breaths or simple tidal breathing—to inhale the drug from the chamber 220 and exhale out via slots 170 provided in the body 160 of valve 141, into the atmosphere. During tidal breathing, the flow of inhalation exceeds the flow of aerosol droplets from the nebuliser and therefore the user preferentially inhales the stored volume of droplets in the bag 212, thereby tending to empty or partially empty the bag. Should a deep inhalation be taken, and the bag 212 fully collapse, additional air would be entrained through inlet 214 from the nebuliser medication cup which has a one-way valve designed specifically for this purpose during normal use, and pass through the tunnel formed by the shape and configuration of both the V-shaped mounting 118 and the T-shaped mounting 218 forming a tunnel open between the mount inlet 214 and outlet 216.

Slow deep breathing and normal tidal breathing is performed at low flow rates and thus the drug is not sucked towards and impacted at the back of the mouth causing it to be deposited in the pharyngeal region. More of the drug is thus breathed into and distributed in the lungs effectively. During exhalation the valve 141 prevents any exhaled air from reaching the chamber 220. If, however, during prolonged exhalation, the bag 212 does fill completely, the excess aerosol would push the valve 181 open and escape through the slits 170 together with the expired air from the user. The pressure required to open the valve 181 from within would be negligible as the small pressure from the user's exhaled air outside the valve would be dissipated anyway by passing through the slits. The Applicant, on artificially creating and testing this situation on a prototype did not even notice any pressure at the time.

Usefully, the embodiment shown in FIGS. 8 and 9 show a version of the spacer device 210 wherein the bag 212 is rotated by 90 degrees relative to the version shown in FIGS.

6 and 7, i.e. it is rotated about a longitudinal axis of conduit 218.1 to be perpendicular, when viewed from above, with conduit 218.2. This provides additional space saving between the user inhaling on outlet 216 and the medication cup 256 and allows for a larger bag 212 to be used, should this be required. Importantly, rotating the bag 212 does not result in the loss of important visual feedback and monitoring to the user during inhalation and exhalation of the aerosolised drugs 227.

The bag 212 can optionally also include a moveable and/or inflatable figurine on an upper side thereof that is configured to stand erect when the bag 212 is inflated and that collapses when the bag 212 is deflated (not shown). The figurine is particularly directed to providing incentive and positive feedback to children while using the spacer device 10 to both entertain them and confirm that they are breathing correctly. In general, the bag may feature representations 180, 280 of, e.g. children's characters or merchandising to assist in making children less apprehensive when using the device 110, 220.

The mouthpiece configurations in this invention allow the escape valve to be advantageously placed so as not to blow exhaled air into the user's face as is the case with most current standard nebulisers.

The low resistance to flow and easy collapsibility of the bag 212 provides effortless breathing and the full capacity to make any changes to flow and/or breathing pattern without any impediment.

Furthermore, the Applicant has identified the following advantages associated with the invention. The metallic nature of the frame (body) 118 and bag 112 removes the potential for static electricity to cause particles to adhere to the interior walls and be retained in the spacer device 110. The bag 112 is detachable and comes in different volumes depending on medical need at the time and user preference. The angle of the entrance ensures that, the droplets from the nebuliser are directed in generally straight lines into the volume of the bag where the micro-dispersed droplets come to rest largely by their own inertia, thereby forming a reservoir cloud or mist of particles suspended in air and ready for inhalation.

In addition, the angle, together with the fact that the entrance is valve-less, ensures that impaction and retention of particles against solid walls and surfaces, is minimised.

It is important to note that various types of extraneous mouthpieces (not shown) can be added to the outlet 116 depending on user or condition requirements. This would include a facemask, if required.

The inferior positioning of the collapsible chamber 220 allows for a larger space (volume) to be used without significantly increasing intrusiveness to the user. Larger volumes in chamber 220 are generally more efficient in drug delivery allowing better dispersal of drug particle droplets 227 and less inclination for impaction of drug particle droplets 227 on side walls, especially in the first embodiment of the spacer device 110 described herein.

Essentially, the total amount of drug emitted from the nebuliser medication cup 256 into the bag 212 is captured within the system and made available for unimpeded inhalation into the lungs with losses minimised at every step along the way.

In addition, during use the amount of bag 220 movement is an important indicator as to the amount of medication 227 being inhaled. This provides important visual qualitative and quantitative functional feedback to the user and/or observer and has been shown to be critical in promoting comforting reassurance and confidence in the device, optimising use, and promoting adherence with treatment. Critically, the current invention device provides the user full control over breathing patterns and flow rate at all times, ideally using slow deep inhalations, regularly or at intervals, or using tidal flows with normal breathing. Low flow rates have been shown to minimize the amount of drug impacting and being retained in the mouth, pharynx and glottic area, while at the same time, ensuring that inhalant drug droplets or particles entering the airway are deposited more evenly through the lung, delivered to more peripheral parts of the lung, and penetrate better into diseased areas where they are needed most As such, the device of the invention, when compared to other inhalation devices, demonstrates:

Improved efficiency of drug delivery to the airways;
Environmental contamination concerns from aerosol loss during exhalation eliminated
Static electricity as wall particle impaction leading to drug being retained in the device not being a significant issue;
Full control of breathing pattern and/or flow rate;
Simplicity and improved ease of use;
Valuable visual functional feedback and reassurance to the user regarding performance during the manoeuvre; and
Low cost.

In addition, all these benefits are amplified in situations where achieving efficient drug delivery is usually most difficult, such as in very young or old users, users who are very ill (such as during a severe asthma attack), or in users with chronic lung disease and damaged airways.

In final summary, the invention herein described utilises the concept of a low resistance, closed-circuit, anti-static, collapsible chamber to produce a device which allows a relaxed normal or low flow rate and breathing pattern during inhalation of aerosolised drugs. These features are particularly beneficial when compared to current devices that the inventor is aware of, particularly when it comes to improved delivery efficiency, simplicity of use, and versatility.

In addition, all these benefits feature most prominently in situations where efficient drug delivery is also most difficult to achieve, such as in very young or old users, users who are very ill (such as during a severe asthma attack), or in users with chronic lung disease and damaged airways. Improved delivery efficiency will reduce wastage and improve cost-effectiveness of expensive nebulised drug formulations such is inhaled gene therapy, vaccinations, alpha 1-antitrypsin, and other biological compounds.

The major shortcoming found in all current standard nebulisers is the loss of at least 50% of the dose to the outside atmosphere during exhalation. As mentioned, this leads to (1) poor drug delivery, and (2) environmental contamination concerns. In light of the above exemplified embodiments, the results of an experiment performed using the invention described herein will now be provided where the experiment confirms that the invention eliminated virtually all of the aerosol loss during exhalation, and not only does this allay concerns of environmental contamination, but also resulted in a greater than 250% increase in emitted drug delivered from the outlet of the device.

Experiment 1

Aim: To compare aerosol delivery and wastage following nebulisation of Salbutamol over 10 minutes through a Pari LC Plus nebuliser alone compared to a Pari LC Plus nebuliser combined with our spacer invention.

Methods: A 100 microgram dose of Salbutamol nebuliser formulation was nebulised over 8 minutes using a standard Pari LC Plus nebuliser.

A breathing simulator set at an adult breathing pattern was connected to the device outlet Filters were set at: (1) the device outlet to measure the amount of Salbutamol delivered to the "mouth" of the simulator; and, (2) at the exhalation valve on the mouthpiece to measure salbutamol wastage due to drug loss during exhalation.

The amount of Salbutamol trapped on the filters was measured using the standardised HPLC method.

The experiment was repeated with the Pari LC Plus combined with the invention with the filters measuring dose delivered from the outlet of the invention and wastage from the relief valve on the mouthpiece.

Figure 12:
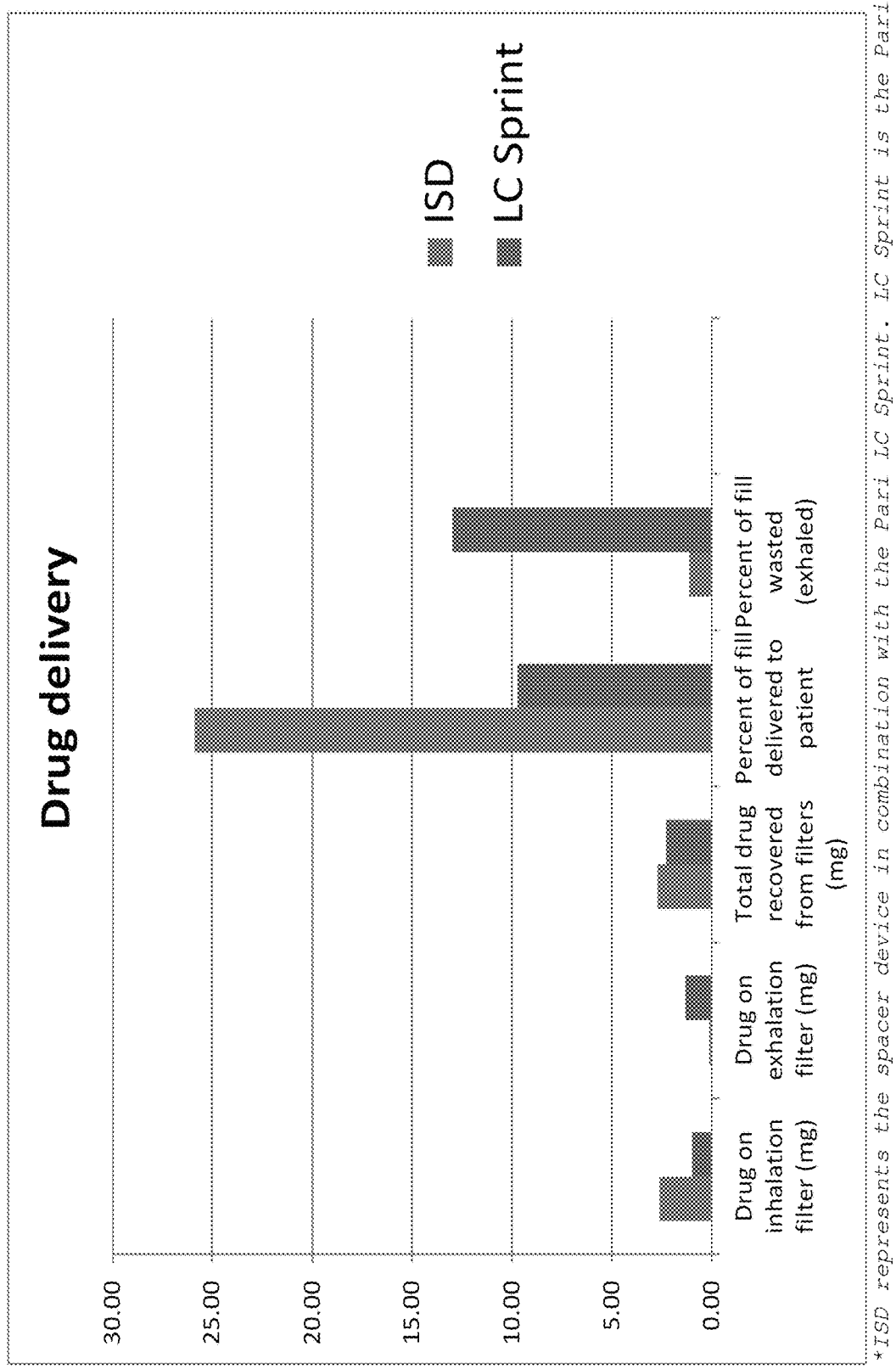
FIG. 12 shows the experimental results of aerosol delivery and wastage following nebulisation of Salbutamol.

Results:

The results are displayed graphically in FIG. 12.

(1) The percentage of dose delivered using the invention together with the Pari LC Plus over the 8-minute nebulisation period was 26% compared to 9.7% delivered by the Pari LC Plus alone. This represents a >250% increase in drug delivery which is in the range of—if not better than—the delivery efficiency of intelligent nebulisers.

(2) The percentage of wastage during exhalation using the invention was negligible at 1.1%, which represents only a small fraction (1/25th) of the dose delivered over the same period. On the other hand, using the Pari LC Plus alone, 12.8% of the dose was measured as wasted during exhalation—more than the 9.7% delivered to the "mouth" during the same period. This is typical of standard nebulisers with more drug wasted than delivered.

Conclusion: The invention effectively minimises drug loss during exhalation thereby virtually eliminating wastage and increasing drug delivery by more than 250%. In turn, this alleviates concerns regarding environmental contamination with wasted aerosolised drug.

Additional preliminary experiments have been performed using a prototype of the invention producing similar results, including a Tc-99 labelled radio-labelled inhalation deposition study where the experiment demonstrated that the Invention paired with a Pari LC Plus nebuliser, showed equivalent Delivery Efficiency (DE) to an Akita Intelligent Nebuliser tested using the same protocol.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth. In the example embodiments, well-known processes, well-known device structures, and well-known technologies are not described in detail, as such will be readily understood by the skilled addressee.

The use of the terms "a", "an", "said", "the", and/or similar referents in the context of describing various embodiments (especially in the context of the claimed subject matter) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. As used herein, the term "and/or" includes any and all combinations of one or more of the associated listed items. No language in the specification should be construed as indicating any non-claimed subject matter as essential to the practice of the claimed subject matter.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

It is to be appreciated that reference to "one example" or "an example" of the invention, or similar exemplary language (e.g., "such as") herein, is not made in an exclusive sense. Various substantially and specifically practical and useful exemplary embodiments of the claimed subject matter are described herein, textually and/or graphically, for carrying out the claimed subject matter.

Accordingly, one example may exemplify certain aspects of the invention, whilst other aspects are exemplified in a different example. These examples are intended to assist the skilled person in performing the invention and are not intended to limit the overall scope of the invention in any way unless the context clearly indicates otherwise. Variations (e.g. modifications and/or enhancements) of one or more embodiments described herein might become apparent to those of ordinary skill in the art upon reading this application. The inventor(s) expects skilled artisans to employ such variations as appropriate, and the inventor(s) intends for the claimed subject matter to be practiced other than as specifically described herein.

The invention claimed is:

1. A spacer device for delivery of a drug via a nebuliser device, the spacer device comprising:

a body having an inlet and an outlet opposed from the inlet, the body being in the form of a V-shaped mounting formed by the opposing inlet and outlet intersecting at an angle along their respective longitudinal axes where the angle creates a V which defines an arc of between 30 and 170 degrees;

a demountable, flexible bag attached to the body, the bag and body together defining a chamber, such that the inlet and outlet are in fluid flow communication with the chamber;

wherein the inlet is configured for operative connection to the nebuliser device containing the drug to be inhaled;

wherein the V-shaped mounting includes a V-shaped interior surface, and has a lower perimeter formed by merging of inferior and lateral aspects of the opposed inlet and outlet, said perimeter being generally oval in shape;

wherein the outlet includes a mouthpiece that is received on, in, or around the outlet and is configured to be operatively received by a user's mouth;

wherein the body, inlet, outlet, and/or bag is configured to prevent a static electricity charge by being made of electrically conductive material or treated with a non-static agent to impede deposition thereon of the drug to be inhaled;

wherein the flexible bag serves as reservoir to allow for the formation therewithin of a cloud or mist of the drug to be inhaled upon activation of the nebuliser device, the flexible bag being configured to be repeatedly inflatable and deflatable commensurate with a breathing pattern of said user, during use, in order to accommodate breathing and provide visual feedback of drug inhalation during such said breathing;

wherein the outlet and/or mouthpiece is configured to control fluid flow between the reservoir and the user's mouth and fluid flow from the user's mouth to the outside atmosphere by preventing entrainment of exhaled air into the reservoir from the outlet when the pressure of the exhaled air entering the outlet exceeds the pressure of the air within the chamber and preventing escape of the drug from the nebuliser to the exterior environment; and wherein the bag is configured to spontaneously adopt a shape of an open inflated/distended position through shape or material memory and to collapse during inhalation.

2. The spacer device of claim 1, wherein the bag is made of a metallised polymer film or aluminium foil.

3. The spacer device of claim 1, wherein the inlet comprises a mount defining an inlet passage for sealingly engaging with an exit port of the nebuliser, the inlet passage surrounded by a sealing collar configured to seal against the exit port.

4. The spacer device of claim 1, wherein the outlet and/or mouthpiece is configured to control fluid flow by including or defining a valve to impede air exhaled by the user from entering the chamber, and to open selectively to the outside atmosphere when the pressure within the outlet and/or mouthpiece exceeds a pre-determined value.

5. The spacer device of claim 4, wherein the valve comprises a body including:

an inlet through which medication from the chamber is receivable;

an outlet which exits to the atmosphere;

a passageway connecting the inlet and outlet; and at least one selectively activatable occlusion member that prevents the entrainment of exhaled air into the spacer device from the outlet when the pressure of the exhaled air entering the outlet exceeds the pressure of the air within the chamber.

6. The spacer device of claim 5, wherein the at least one occlusion member is in the form of at least one flexible flap for occluding the passageway defined through the body of the valve, the flap in the form of a soft, flexible filament, fabric, or sheet attached to the body of the valve or attached to a central spine which serves to bifurcate the passageway defined between the inlet and outlet of the valve body.

7. The spacer device of claim 6, wherein the outlet includes at least one escape passage defined herein in the body for the escape of air upon occlusion of the passageway of the body by the occlusion member.

8. The spacer device of claim 7, wherein the at least one escape passage is in the form of a passage defined within the body that allows for the exit of air through at least one aperture provided within a radially extending formation that extends at least partially around an outer surface of the body.

9. The spacer device of claim 8, wherein the at least one aperture is in the form of a slot provided within the radially extending formation, a size, shape, number and dimension of the slot configured to accommodate flow rates of medication, breathing frequency, and/or exhalation force of the user, to minimise the effects of exhalation and facilitate inhalation of medication contained within the bag.

10. The spacer device of claim 9, wherein the at least one aperture is defined within the radially extending formation and has one or more slot-occluding flap members in the form of one or more flexible flap members applied externally to each slot which serve to occlude the at least one apertures during inhalation, and open to allow exhaled air to pass through the at least one aperture and past the one or more flexible flap members, to the exterior environment.

11. The spacer device of claim 1, wherein the arc of the V-shaped mounting is 90 degrees.

12. The spacer device of claim 1, wherein the lower perimeter constitutes the portion of the mounting that receives the demountable bag.

13. The spacer device of claim 1, wherein the interior of the V-shaped mounting is shaped and dimensioned to define a cavity that provides a passage for flow of air and/or medication between the inlet and the bag and between the bag and the mouthpiece, the interior of the V-shaped cavity sized and dimensioned to receive the bag when the bag is folded into the cavity for portability purposes.

14. The spacer device of claim 1, wherein a ratio of major and minor axes of the oval lower perimeter is between 1.01:1 and 6:1.

15. The spacer device of claim 14, wherein the ratio is 1.38:1.

16. The spacer device of claim 1, wherein the bag has an opening including a collar that is shaped and dimensioned to fit securely to the lower perimeter of the body of the spacer device to facilitate releasable attachment of the bag to the body of the spacer device, the collar extending along an upper periphery of the bag opening and extending at least partially around the opening of the bag.

17. The spacer device of claim 16, wherein the bag opening is biased towards an open, distended position by way of being made of a resiliently flexible material.

18. The spacer device of claim 1, wherein the bag is provided with a peripherally extending, resiliently flexible seam which serves to resist collapse of the bag during inhalation and exhalation.

19. The spacer device of claim 1, wherein a size, shape and/or distensibility of said bag is configured relative to a lung volume and inhalation capacity and/or capabilities of the user, the medical needs at the time of use, and/or the user preference.

* * * * *